US005766860A

United States Patent [19]

Terman et al.

[11] Patent Number: 5,766,860
[45] Date of Patent: Jun. 16, 1998

[54] SCREENING METHOD USING A RECOMBINANT KINASE INSERT DOMAIN CONTAINING RECEPTOR AND GENE ENCODING SAME

[75] Inventors: Bruce Israel Terman, Monroe; Miguel Eduardo Carrion, Spring Valley, both of N.Y.

[73] Assignee: American Cyanamid Company, Madison, N.J.

[21] Appl. No.: 810,116

[22] Filed: Feb. 25, 1997

Related U.S. Application Data

[62] Division of Ser. No. 930,548, Nov. 23, 1992.

[51] Int. Cl.⁶ ................................................ G01N 33/53
[52] U.S. Cl. ..................... 435/7.2; 435/7.8; 435/69.1; 435/325; 435/361; 436/501
[58] Field of Search ................. 536/23.5, 24.31; 435/69.1, 172.1, 172.3, 325, 361, 252.3, 320.1, 183, 7.1, 7.2, 7.8; 530/350, 351, 399; 935/9, 19; 436/501

[56] References Cited

U.S. PATENT DOCUMENTS 4,743,679  5/1988  Cohen et al. ............................. 530/350
4,966,841  10/1990 Riley ........................................ 435/69.1
5,283,354  2/1994  Lemischka ............................... 536/23.5

OTHER PUBLICATIONS

A. Bikfalvi et al., J. Cellular Physiology 149(1):50–59, Oct. 1991.
L.B. Jakeman et al., J. Clin. Invest. 89(1):244–253, Jan. 1992.
T. Cohen et al., Growth Factors 7(2):131–138, 1992.
R.G.K. Gronwald et al., PNAS 85:3435–3439, May 1988.
J.U. Bowie et al., Science 247:1306, Mar. 16, 1990.
M. Shibuya et al., Oncogene 5:519–524, 1990.

Primary Examiner—Stephen Walsh
Assistant Examiner—L. Spector
Attorney, Agent, or Firm—Elizabeth M. Barnhard; Alan M. Gordon

[57] ABSTRACT

A DNA sequence encoding a novel human growth factor receptor referred to as a type III receptor tyrosine kinase is described. The amino acid sequence of the receptor is also described. The receptor has a sequence which is similar to that of the kinase domains of known type III receptor tyrosine kinases, but which is unique in its kinase insert domain sequence. The receptor binds specifically to the vascular endothelial cell growth factor.

1 Claim, 28 Drawing Sheets

FIG. 2

PRIMER 1

RECEPTOR

```
PDGF    AAC CTG TTG GGG GCC TGC ACC
ckit        T   A           A
CSF         T   A
CSF                 C               G
FGF
```

PRIMER 1    GTCGAC AAC CTG TTG GGG GCC TGC AAC
                           T           A

PRIMER 2

RECEPTOR

```
PDGF    CAC AGA GAC CTG GCG GCT AGG AAC GTG CT
ckit            T       GA  C   A   T       A
CSF         C G     A   GC  C T
CSF         C           A   C   C       T   C
FGF
```

CONSENSUS  CAC AGA GAC CTG GCC GCT AGI AAC GTG CT
                   T            C           T

PRIMER 2   GAATTC AG CAC GTT ICT AGC CGC CAG GTC TCT GTG
                           T       G   T                G

```
ATG GAG AGC AAG GTG CTG CTG GCC GTC GCC CTG TGG CTC TGC GTG GAG ACC CGG
Met Glu Ser Lys Val Leu Leu Ala Val Ala Leu Trp Leu Cys Val Glu Thr Arg>

GCC GCC TCT GTG GGT TTG CCT AGT GTT TCT CTT GAT CTG CCC AGG CTC AGC ATA
Ala Ala Ser Val Gly Leu Pro Ser Val Ser Leu Asp Leu Pro Arg Leu Ser Ile>

CAA AAA GAC ATA CTT ACA ATT AAG GCT ACA ACT CTT CAA ATT ACT TGC AGG
Gln Lys Asp Ile Leu Thr Ile Lys Ala Thr Thr Leu Gln Ile Thr Cys Arg>

GGA CAG AGG GAC TTG GAC TGG CTT TGG CCC AAT AAT CAG AGT GGC AGT GAG CAA
Gly Gln Arg Asp Leu Asp Trp Leu Trp Pro Asn Asn Gln Ser Gly Ser Glu Gln>

AGG GTG GAG GTG ACT GAG TGC AGC GAT GGC CTC TTC TGT AAG ACA CTC ACA ATT
Arg Val Glu Val Thr Glu Cys Ser Asp Gly Leu Phe Cys Lys Thr Leu Thr Ile>

CCA AAA GTG ATC GGA AAT GAC ACT GGA GCC TAC AAG TGC TTC TAC CGG GAA ACT
Pro Lys Val Ile Gly Asn Asp Thr Gly Ala Tyr Lys Cys Phe Tyr Arg Glu Thr>
```

FIG. 7A

```
GAC TTG GCC TCG GTC ATT TAT GTC ATT CAA GAT TAC AGA TCT CCA TTT ATT
Asp Leu Ala Ser Val Ile Tyr Val Tyr Val Gln Asp Tyr Arg Ser Pro Phe Ile>

GCT TCT GTT AGT GAC CAA CAT GGA GTC GTG TAC ATT ACT GAG AAC AAA AAC AAA
Ala Ser Val Ser Asp Gln His Gly Val Val Tyr Ile Thr Glu Asn Lys Asn Lys>

ACT GTG GTG ATT CCA TGT CTC GGG TCC ATT TCA AAT CTC AAC GTG TCA CTT TGT
Thr Val Val Ile Pro Cys Leu Gly Ser Ile Ser Asn Leu Asn Val Ser Leu Cys>

GCA AGA TAC CCA GAA AAG AGA TTT GTT CCT GAT GGT AAC AGA ATT TCC TGG GAC
Ala Arg Tyr Pro Glu Lys Arg Phe Val Pro Asp Gly Asn Arg Ile Ser Trp Asp>

AGC AAG AAG GGC TTT ACT ATT CCC AGC TAC ATG ATC AGC TAT GCT GGC ATG GTC
Ser Lys Lys Gly Phe Thr Ile Pro Ser Tyr Met Ile Ser Tyr Ala Gly Met Val>

TTC TGT GAA GCA AAA ATT AAT GAT GAA AGT TAC CAG TCT ATT ATG TAC ATA GTT
Phe Cys Glu Ala Lys Ile Asn Asp Glu Ser Tyr Gln Ser Ile Met Tyr Ile Val>
```

FIG. 7B

```
650       660       670       680       690       700
 *         *         *         *         *         *
GTC GTT GTA GGG TAT AGG ATT TAT GAT GTG GTT CTG AGT CCG TCT CAT GGA ATT
Val Val Val Gly Tyr Arg Ile Tyr Asp Val Val Leu Ser Pro Ser His Gly Ile>

710       720       730       740       750
 *         *         *         *         *
GAA CTA TCT GTT GGA GAA AAG CTT GTC TTA GTT CTT AAT TGT ACA GCA AGA ACT GAA CTA
Glu Leu Ser Val Gly Glu Lys Leu Val Leu Asn Cys Thr Ala Arg Thr Glu Leu>

760       770       780       790       800       810
 *         *         *         *         *         *
AAT GTG GGG ATT GAC TTC AAC TGG GAA TAC CCT TCT TCG AAG CAT CAG CAT AAG
Asn Val Gly Ile Asp Phe Asn Trp Glu Tyr Pro Ser Ser Lys His Gln His Lys>

820       830       840       850       860
 *         *         *         *         *
AAA CTT GTA AAC CGA GAC CTA AAA ACC CAG TCT GGG AGT GAG ATG AAG AAA TTT
Lys Leu Val Asn Arg Asp Leu Lys Thr Gln Ser Gly Ser Glu Met Lys Lys Phe>

870       880       890       900       910
 *         *         *         *         *
TTG AGC ACC TTA ACT ATA GAT GGT GTA ACC CGG AGT GAC CAA GGA TTG TAC ACC
Leu Ser Thr Leu Thr Ile Asp Gly Val Thr Arg Ser Asp Gln Gly Leu Tyr Thr>

920       930       940       950       960       970
 *         *         *         *         *         *
TGT GCA GCA TCC AGT GGG CTG ATG ACC AAG AAG AAC AGC ACA TTT GTC AGG GTC
Cys Ala Ala Ser Ser Gly Leu Met Thr Lys Lys Asn Ser Thr Phe Val Arg Val>
```

FIG. 7C

```
                              980                 990                1000               1010               1020
                               *                   *                  *                  *                  *
                     CAT GAA AAA CCT TTT GTT GCT TTT GGA AGT GGC ATG GAA TCT CTG GTG GAA GCC
                     His Glu Lys Pro Phe Val Ala Phe Gly Ser Gly Met Glu Ser Leu Val Glu Ala>

1030               1040               1050               1060               1070               1080
                               *                   *                  *                  *                  *                  *
                     ACG GTG GGG GAG CGT GTC AGA ATC CCT GCG AAG TAC CTT GGT TAC CCA CCC CCA
                     Thr Val Gly Glu Arg Val Arg Ile Pro Ala Lys Tyr Leu Gly Tyr Pro Pro Pro>

1090               1100               1110               1120               1130
                               *                   *                  *                  *                  *
                     GAA ATA AAA TGG TAT AAA AAT GGA ATA CCC CTT GAG TCC AAT CAC ACA ATT AAA
                     Glu Ile Lys Trp Tyr Lys Asn Gly Ile Pro Leu Glu Ser Asn His Thr Ile Lys>

1140               1150               1160               1170               1180
                               *                   *                  *                  *                  *
                     GCG GGG CAT GTA CTG ACG ATT ATG GAA GTG AGT GAA AGA GAC ACA GGA AAT TAC
                     Ala Gly His Val Leu Thr Ile Met Glu Val Ser Glu Arg Asp Thr Gly Asn Tyr>

1190               1200               1210               1220               1230               1240
                               *                   *                  *                  *                  *                  *
                     ACT GTC ATC CTT ACC AAT CCC ATT TCA AAG GAG AAG CAG AGC CAT GTG GTC TCT
                     Thr Val Ile Leu Thr Asn Pro Ile Ser Lys Glu Lys Gln Ser His Val Val Ser>

1250               1260               1270               1280               1290
                               *                   *                  *                  *                  *
                     CTG GTT GTG TAT GTC CCA CCC CAG ATT GGT GAG AAA TCT CTA ATC TCT CCT GTG
                     Leu Val Val Tyr Val Pro Pro Gln Ile Gly Glu Lys Ser Leu Ile Ser Pro Val>
```

FIG. 7D

```
                1300                  1310                  1320                  1330                  1340                  1350
                 *                     *                     *                     *                     *                     *
GAT TCC TAC CAG TAC GGC ACC ACT CAA ACG CTG ACA TGT ACG GTC TAT GCC ATT
Asp Ser Tyr Gln Tyr Gly Thr Thr Gln Thr Leu Thr Cys Thr Val Tyr Ala Ile>

1360                  1370                  1380                  1390                  1400
                 *                     *                     *                     *                     *
CCT CCC CCG CAT CAC ATC CAC TGG TAT TGG CAG TTG GAG GAA GAG TGC GCC AAC
Pro Pro Pro His His Ile His Trp Tyr Trp Gln Leu Glu Glu Glu Cys Ala Asn>

1410                  1420                  1430                  1440                  1450
                 *                     *                     *                     *                     *
GAG CCC AGC CAA GCT GTC TCA GTG ACA AAC CCA TAC CCT TGT GAA GAA TGG AGA
Glu Pro Ser Gln Ala Val Ser Val Thr Asn Pro Tyr Pro Cys Glu Glu Trp Arg>

1460                  1470                  1480                  1490                  1500                  1510
       *                     *                     *                     *                     *                     *
AGT GTG GAG GAC TTC CAG GGA AAT AAA ATT GAA GTT AAT AAA AAT CAA TTT
Ser Val Glu Asp Phe Gln Gly Asn Lys Ile Glu Val Asn Lys Asn Gln Phe>

1520                  1530                  1540                  1550                  1560
                 *                     *                     *                     *                     *
GCT CTA ATT GAA GGA AAA AAC AAA ACT GTA AGT ACC CTT GTT ATC CAA GCG GCA
Ala Leu Ile Glu Gly Lys Asn Lys Thr Val Ser Thr Leu Val Ile Gln Ala Ala>

1570                  1580                  1590                  1600                  1610                  1620
       *                     *                     *                     *                     *                     *
AAT GTG TCA GCT TTG TAC AAA TGT GAA GCG GTC AAC AAA GTC GGG AGA GGA GAG
Asn Val Ser Ala Leu Tyr Lys Cys Glu Ala Val Asn Lys Val Gly Arg Gly Glu>
```

FIG. 7E

```
                        1630                    1640                    1650                    1660                    1670
                         *                       *                       *                       *                       *
AGG GTG ATC TCC TTC CAC GTG ACC AGG GGT CCT GAA ATT ACT TTG CAA CCT GAC
Arg Val Ile Ser Phe His Val Thr Arg Gly Pro Glu Ile Thr Leu Gln Pro Asp>

1680                    1690                    1700                    1710                    1720
       *                       *                       *                       *                       *
ATG CAG CCC ACT GAG CAG GAG AGC GTG TCT TTG TGG TGC ACT GCA GAC AGA TCT
Met Gln Pro Thr Glu Gln Glu Ser Val Ser Leu Trp Cys Thr Ala Asp Arg Ser>

1730                    1740                    1750                    1760                    1770                    1780
 *                       *                       *                       *                       *                       *
ACG TTT GAG AAC CTC ACA TGG TAC AAG CTT GGC CCA CAG CCT CTG CCA ATC CAT
Thr Phe Glu Asn Leu Thr Trp Tyr Lys Leu Gly Pro Gln Pro Leu Pro Ile His>

1790                    1800                    1810                    1820                    1830
       *                       *                       *                       *                       *
GTG GGA GAG TTG CCC ACA CCT GTT TGC AAG AAC TTG GAT ACT CTT TGG AAA TTG
Val Gly Glu Leu Pro Thr Pro Val Cys Lys Asn Leu Asp Thr Leu Trp Lys Leu>

1840                    1850                    1860                    1870                    1880                    1890
       *                       *                       *                       *                       *                       *
AAT GCC ACC ATG TTC TCT AAT AGC ACA AAT GAC ATT TTG ATC ATG GAG CTT AAG
Asn Ala Thr Met Phe Ser Asn Ser Thr Asn Asp Ile Leu Ile Met Glu Leu Lys>

1900                    1910                    1920                    1930                    1940
       *                       *                       *                       *                       *
AAT GCA TCC TTG CAG GAC CAA GGA GAC TAT GTC TGC CTT GCT CAA GAC AGG AAG
Asn Ala Ser Leu Gln Asp Gln Gly Asp Tyr Val Cys Leu Ala Gln Asp Arg Lys>
```

FIG. 7F

```
              1950            1960            1970            1980            1990
               *               *               *               *               *
ACC AAG AAA AGA CAT TGC GTG GTC AGG CAG CTC ACA GTC CTA GAG CGT GTG GCA
Thr Lys Lys Arg His Cys Val Val Arg Gln Leu Thr Val Leu Glu Arg Val Ala>

2000            2010            2020            2030            2040            2050
   *               *               *               *               *               *
CCC ACG ATC ACA GGA AAC CTG GAG AAT CAG ACA ACG ACA AGT ATT GGG GAA AGC ATC
Pro Thr Ile Thr Gly Asn Leu Glu Asn Gln Thr Thr Thr Ser Ile Gly Glu Ser Ile>

2060            2070            2080            2090            2100
   *               *               *               *               *
GAA GTC TCA TGC ACG GCA TCT GGG AAT CCC CCT CCA CAG ATC ATG TGG TTT AAA
Glu Val Ser Cys Thr Ala Ser Gly Asn Pro Pro Pro Gln Ile Met Trp Phe Lys>

2110            2120            2130            2140            2150            2160
  *               *               *               *               *               *
GAT AAT GAG ACC ATC CGC AGA GTG CTT GTA GAA GAC TCA GGC ATT GTA TTG AAG GAT GGG AAC CGG
Asp Asn Glu Thr Ile Arg Arg Val Leu Val Glu Asp Ser Gly Ile Val Leu Lys Asp Gly Asn Arg>

2170            2180            2190            2200            2210
            *               *               *               *               *
AAC CTC ACT ATC CGC AGA GTG AGG AAG GAG GAC GAG GGC CTC TAC ACC TGC CAG
Asn Leu Thr Ile Arg Arg Val Arg Lys Glu Asp Glu Gly Leu Tyr Thr Cys Gln>

2220            2230            2240            2250            2260
   *               *               *               *               *
GCA TGC AGT GTT CTT GGC TGT GCA AAA GTG GAG GCA TTT TTC ATA ATA GAA GGT
Ala Cys Ser Val Leu Gly Cys Ala Lys Val Glu Ala Phe Phe Ile Ile Glu Gly>
```

FIG. 7G

```
                          2280        2290        2300        2310        2320
                           *           *           *           *           *
GCC CAG GAA AAG ACG AAC TTG GAA ATC ATT ATT CTA GTA GGC ACG GTG ATT
Ala Gln Glu Lys Thr Asn Leu Glu Ile Ile Ile Leu Val Gly Thr Thr Val Ile>

2330        2340        2350        2360        2370
       *           *           *           *           *
GCC ATG TTC TTC TGG CTA CTT CTT GTC ATC CTA GGG ACC GTT AAG CGG GCC
Ala Met Phe Phe Trp Leu Leu Leu Val Ile Leu Gly Thr Val Lys Arg Ala>

2380        2390        2400        2410        2420        2430
              *           *           *           *           *           *
AAT GGA GGG GAA CTG AAG ACA GGC TAC TTG TCC ATC GTC ATG GAT CCA GAT GAA
Asn Gly Gly Glu Leu Lys Thr Gly Tyr Leu Ser Ile Val Met Asp Pro Asp Glu>

2440        2450        2460        2470        2480
              *           *           *           *           *
CTC CCA TTG GAT GAA CAT TGT GAA CGA CTG CCT TAT GAT GCC AGC AAA TGG GAA
Leu Pro Leu Asp Glu His Cys Glu Arg Leu Pro Tyr Asp Ala Ser Lys Trp Glu>

2490        2500        2510        2520        2530
              *           *           *           *           *
TTC CCC AGA GAC CGG CTG AAC CTA GGT AAG CCT CTT GGC CGT GGT GCC TTT GGC
Phe Pro Arg Asp Arg Leu Asn Leu Gly Lys Pro Leu Gly Arg Gly Ala Phe Gly>

2540        2550        2560        2570        2580        2590
       *           *           *           *           *           *
CAA GAG ATT GAA GCA GAT GCC TTT GGA ATT GAC AAG ACA GCA ACT TGC AGG ACA
Gln Glu Ile Glu Ala Asp Ala Phe Gly Ile Asp Lys Thr Ala Thr Cys Arg Thr>
```

FIG. 7H

```
                2600      2610      2620      2630      2640
                 *         *         *         *         *
            GTA GCA GTC AAA ATG TTG AAA GAA GGA GCA ACA CAC AGT GAG CAT CGA GCT CTC
            Val Ala Val Lys Met Leu Lys Met Leu Lys Glu Gly Ala Thr His Ser Glu His Arg Ala Leu>

2650      2660      2670      2680      2690      2700
       *         *         *         *         *         *
  ATG TCT GAA CTC AAG ATC CTC ATT CAT ATT GGT CAC CAT CTC AAT GTC AAC
  Met Ser Glu Leu Lys Ile Leu Ile His Ile Gly His His Leu Asn Val Asn>

2710      2720      2730      2740      2750
             *         *         *         *         *
      CTT CTA GGT GCC TGT ACC AAG CCA GGA GGG CCA CTC ATG ATT GTG GAA TTC
      Leu Leu Gly Ala Cys Thr Lys Pro Gly Gly Pro Leu Met Val Ile Val Glu Phe>

2760      2770      2780      2790      2800
   *         *         *         *         *
  TGC AAA TTT GGA AAC CTG TCC ACT TAC CTG AGG AGC AAG AGA AAT GAA TTT GTC
  Cys Lys Phe Gly Asn Leu Ser Thr Tyr Leu Arg Ser Lys Arg Asn Glu Phe Val>

2810      2820      2830      2840      2850      2860
       *         *         *         *         *         *
  CCC TAC AAG ACC AAA GGG GCA CGA TTC CGT CAA GGG AAA GAC TAC GTT GGA GCA
  Pro Tyr Lys Thr Lys Gly Ala Arg Phe Arg Gln Gly Lys Asp Tyr Val Gly Ala>

2870      2880      2890      2900      2910
       *         *         *         *         *
  ATC CCT GTG GAT CTG AAA CGG CGC TTG GAC AGC ATC ACC AGT AGC CAG AGC TCA
  Ile Pro Val Asp Leu Lys Arg Arg Leu Asp Ser Ile Thr Ser Ser Gln Ser Ser>
```

FIG. 7I

```
      2920          2930          2940          2950          2960          2970
        *             *             *             *             *             *
GCC AGC TCT GGA TTT GTG GAG GAG AAG TCC CTC AGT GAT GTA GAA GAA GAG GAA
Ala Ser Ser Gly Phe Val Glu Glu Lys Ser Leu Ser Asp Val Glu Glu Glu Glu>
              2980          2990          3000          3010          3020
                *             *             *             *             *
GCT CCT GAA GAT CTG TAT AAG GAC TTC CTG ACC TTG GAG CAT CTC ATC TGT TAC
Ala Pro Glu Asp Leu Tyr Lys Asp Phe Leu Thr Leu Glu His Leu Ile Cys Tyr>
      3030          3040          3050          3060          3070
        *             *             *             *             *
AGC TTC CAA GTG GCT AAG GGC ATG GAG TTC TTG GCA TCG CGA AAG TGT ATC CAC
Ser Phe Gln Val Ala Lys Gly Met Glu Phe Leu Ala Ser Arg Lys Cys Ile His>
3080          3090          3100          3110          3120          3130
  *             *             *             *             *             *
AGG GAC CTG GCG GCA CGA AAT ATC CTC TTA TCG GAG AAG AAC GTG GTT AAA ATC
Arg Asp Leu Ala Ala Arg Asn Ile Leu Leu Ser Glu Lys Asn Val Val Lys Ile>
      3140          3150          3160          3170          3180
        *             *             *             *             *
TGT GAC TTT GGC TTG GCC CGG GAT ATT TAT AAA GAT CCA GAT TAT GTC AGA AAA
Cys Asp Phe Gly Leu Ala Arg Asp Ile Tyr Lys Asp Pro Asp Tyr Val Arg Lys>
3190          3200          3210          3220          3230          3240
  *             *             *             *             *             *
GGA GAT GCT CGC CTC CCT TTG AAA TGG ATG GCC CCA GAA ACA ATT TTT GAC AGA
Gly Asp Ala Arg Leu Pro Leu Lys Trp Met Ala Pro Glu Thr Ile Phe Asp Arg>
```

FIG. 7J

```
       3250                3260                3270                3280                3290
        *                   *                   *                   *                   *
GTG TAC ACA ATC CAG AGT GAC GTC TGG TCT TTT GGT GTT TTG CTG TGG GAA ATA
Val Tyr Thr Ile Gln Ser Asp Val Trp Ser Phe Gly Val Leu Leu Trp Glu Ile>

3300                3310                3320                3330                3340
        *                   *                   *                   *                   *
TTT TCC TTA GGT GCT TCT CCA TAT CCT GGG GTA AAG ATT GAT GAA GAA TTT TGT
Phe Ser Leu Gly Ala Ser Pro Tyr Pro Gly Val Lys Ile Asp Glu Glu Phe Cys>

3350                3360                3370                3380                3390                3400
        *                   *                   *                   *                   *                   *
AGG CGA TTG AAA GAA GGA ACT AGA ATG AGG GCC CCT GAT TAT ACT ACA CCA GAA
Arg Arg Leu Lys Glu Gly Thr Arg Met Arg Ala Pro Asp Tyr Thr Thr Pro Glu>

3410                3420                3430                3440                3450
        *                   *                   *                   *                   *
ATG TAC CAG ACC ATG CTG GAC TGC TGG CAC GGG GAG CCC AGT CAG AGA CCC ACG
Met Tyr Gln Thr Met Leu Asp Cys Trp His Gly Glu Pro Ser Gln Arg Pro Thr>

3460                3470                3480                3490                3500                3510
        *                   *                   *                   *                   *                   *
TTT TCA GAG TTG GTG GAA CAT TTG GGA AAT CTC TTG CAA GCT AAT GCT CAG CAG
Phe Ser Glu Leu Val Glu His Leu Gly Asn Leu Leu Gln Ala Asn Ala Gln Gln>

3520                3530                3540                3550                3560
        *                   *                   *                   *                   *
GAT GGC AAA GAC TAC ATT GTT CTT CCG ATA TCA GAG ACT TTG AGC ATG GAA GAG
Asp Gly Lys Asp Tyr Ile Val Leu Pro Ile Ser Glu Thr Leu Ser Met Glu Glu>
```

FIG. 7K

```
                      3570            3580            3590            3600            3610
                       *               *               *               *               *
                      GAT TCT GGA CTC TCT CTG CCT ACC TCA CCT GTT TCC TGT ATG GAG GAG GAA
                      Asp Ser Gly Leu Ser Leu Pro Thr Ser Pro Val Ser Cys Met Glu Glu Glu>

3620            3630            3640            3650            3660            3670
   *               *               *               *               *               *
  GTA TGT GAC CCC AAA TTC CAT TAT GAC AAC ACA GCA GGA ATC AGT CAG TAT CTG
  Val Cys Asp Pro Lys Phe His Tyr Asp Asn Thr Ala Gly Ile Ser Gln Tyr Leu>

3680            3690            3700            3710            3720
                       *               *               *               *               *
                      CAG AAC AGT AAG CGA AAG AGC CGG CCT GTG AGT GTA AAA ACA TTT GAA GAT ATC
                      Gln Asn Ser Lys Arg Lys Ser Arg Pro Val Ser Val Lys Thr Phe Glu Asp Ile>

3730            3740            3750            3760            3770            3780
   *               *               *               *               *               *
  CCG TTA GAA GAA CCA GAA GTA ATC CCA GAT GAC AAC CAG ACG GAC AGT
  Pro Leu Glu Glu Pro Glu Val Ile Pro Asp Asp Asn Gln Thr Asp Ser>

3790            3800            3810            3820            3830
                       *               *               *               *               *
                      GGT ATG GTT CTT GCC TCA GAG CTG AAA ACT TTG GAA GAC AGA ACC AAA TTA
                      Gly Met Val Leu Ala Ser Glu Leu Lys Thr Leu Glu Asp Arg Thr Lys Leu>

3840            3850            3860            3870            3880
   *               *               *               *               *
  TCT CCA TCT TTT GGT GGA ATG GTG CCC AGC AAA AGC AGG GAG TCT GTG GCA TCT
  Ser Pro Ser Phe Gly Gly Met Val Pro Ser Lys Ser Arg Glu Ser Val Ala Ser>

FIG. 7L
```

```
       3890       3900       3910       3920       3930       3940
        *          *          *          *          *          *
       GAA GGC TCA AAC CAG ACA AGC GGC TAC CAG TCC GGA TAT CAC TCC GAT GAC ACA
       Glu Gly Ser Asn Gln Thr Ser Gly Tyr Gln Ser Gly Tyr His Ser Asp Asp Thr>

3950       3960       3970       3980       3990
        *          *          *          *          *
       GAC ACC ACC GTG TAC TCC AGT GAG GAA GCA GAA CTT TTA AAG CTG ATA GAG ATT
       Asp Thr Thr Val Tyr Ser Ser Glu Glu Ala Glu Leu Leu Lys Leu Ile Glu Ile>

4000       4010       4020       4030       4040       4050
        *          *          *          *          *          *
       GGA GTG CAA ACC GGT AGC ACA GCC CAG ATT CTC CAG CCT GAC ACG GGG ACC ACA
       Gly Val Gln Thr Gly Ser Thr Ala Gln Ile Leu Gln Pro Asp Thr Gly Thr Thr>

4060       4070
        *          *
       CTG AGC TCT CCT CCT GTT TAA ***
       Leu Ser Ser Pro Pro Val ***
```

FIG. 7M

```
KDR    787  GTVKRANGGELKTGYLSIVMDPDELPLDEHCERLPYDASKWEFPRDRLNLGK
ckit   543  L***YLQKPMYEVQWKVVEEINGNNYVIDPTQ****H-*****N-*SF**
CSF1   536  LLY*YKQKPKYQVRWKIIESYEGNSYTFIDPTQ****NE-*****NN*QF**
PDGF   522  MLWQKKPRYEIRWKVIESVSSDGHEYIYVDPVQ****-ST******QLV**R
                                      * **
KDR    839  PLGRGAFGQEIEADAFGIDKTATCRTVAVKMLKEGATHSEHRALMSELKILI
ckit   594  TA**KVVAET*Y*LI*SDAAM*******PS*HLT*RE******V*S
CSF1   587  TAKVVT*LG*EDAVLK*******ST*HAD*KE******MS
PDGF   573  TSVVT*H*LSHSQATMK*******ST*RSS*KQS******MS KDR    891  HIGHHLNVVNLLGACTKPGGPLMVIVEFCKFGNLSTYLRSKRNEFVPYKTKG
ckit   646  YL*N*M*I*****I-*TL**T*Y*CY*D*LNFRDS*ICS*QED
CSF1   639  *L*Q*E*I*******H-***VL**T*Y*CY*D*LNF**R*AEAMLGPSLSP
PDGF   625  *L*P********-*IYI*T*Y*RY*D*VD**HRNKHT*LQRHSNK KDR    943  ARFRQGKDYVGAIPVDLKRRLDSIT-SSQSSASSGFVEEKSL-----SDV
ckit   697  HAEA-A-L*KNLLHSKESSCS-DS*N-E----YMDMKPGVS--YVVPT--KA
CSF1   690  GQDPE*GVDYKN*HLEK*YVRRDSGF***GVDTYVEMRPVSTSS-NDSF*EQ
PDGF   676  HCPPSAEL*SN*LP*GFSLPSHLNLTGESDGGYMDMSKDESIDYVPMLDMKG KDR    987  EEEEAPEDLYKDF--------------LTLEHLICYSFQV
ckit   737  D-KRRSVRIGSYI----------ERDVTPAIMEDDELA*D**D*LSF*Y**
CSF1   741  DLDKEDGRPL-------------------E*RD*LHF*S**
PDGF   728  DIKY*DIESPSYMAPYDNYVPSAPERTYRATLINDSPV-*SYTD*VGF*Y**

KDR    1013 AKGMEFLASRKCIHRDLAARNILLSEKNVVKICDFGLARDIYKDPDYVRKGD
```

FIG. 9A

```
ckit  777  -*A*****N************************THGRIT*********KN*SNVN
CSF1  762  *QA*****N************************TNGHVAG********MN*SN*IV**N
PDGF  779  *ND*****N**************************V*ICEGKL********MR*SN*IS**S KDR  1065  ARLPLKWMAPETIFDRVYTIQSDVWSFGVLLWEIFSLGASPYPGVKIDEEFC
ckit  828  ***V*SNCEE**Y*IF******S*MPVKSK*Y
CSF1  814  *****V*****S***C***VQ*****Y*I*******LN****ILVNSK*Y
PDGF  831  *************SNS*TL*I****GT*ELPMNDQ*Y KDR  1117  RRLKEGTRMRAPDYTTPEMYQTMLDCWHGEPSQRPTFSELVEHLGNLLQANA
ckit  880  KMI**FLSEHAPA*DI*KT**DAD*LK****KQIVQLIEKQISEST
CSF1  862  KLV*D*YQ*AQ*AFAPKNI*****QA**AL*,*TH****QQICSF*QEQAQEDR
PDGF  883  NAI*RYAQ*AHASD*I*EI*QKEEKFETPQLL*ER**GEGY KDR  1169  QQDGKDYIVLPISETLSMEEDSGLSLPTSPVSCMEEEVCDPKFHYDNTAGI
ckit  932  NHIYSNLANCSPNRQKPVVDHSVRINSVGSTASSSQPLLVHDDV
CSF1  914  RERDYTNLPSSSRSGG*GSSS*E*EEESSSEHLTCC*QGDIAQPLLQPNNYQ
PDGF  934  KKKYQQVDEEFLRSDHPAILR*QARF*GIHSLRSPLDTSSVLYTAVQPNESD KDR  1213  SQYLQNSKRKSRPVSVKTFEDIPLEEPEVKVIPDDNQTDSGMVLASEELKTL
CSF1  966  FC
PDGF  987  ND*IIPLPDPKPD*ADEGLPEGSPSLASSTLNEVNTSSTISCDSPL*LQEEP KDR  1273  EDRTKLSPSFGGMVPSKSRESVASEGSNQTSGYQSGYHSDDTDTTVYSSEEA
PDGF 1039  QQAEPEAQLEQPQDSGCPGPLAEA*DSFLEQPQD**CPGPLAEAEDSFL

KDR  1325  ELLKLIEIGVQTGSTAQILQPDTGTTLSSPPV
```

FIG. 9B

IDENTIFICATION OF *kdp* mRNA

IDENTIFICATION OF *kdp* GENE
BY SOUTHERN ANALYSIS 1  2  3  4

5,766,860

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
GTCGACAAYC TGTTGGGRGC CTGCAAC                                          27
```

( 2 ) INFORMATION FOR SEQ ID NO:2:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
GAATTCAGCA CKTTNCTRGC YGCCAGGTCT GYGTC                                 35
```

( 2 ) INFORMATION FOR SEQ ID NO:3:

( i ) SEQUENCE CHARACTERISTICS:
        ( A ) LENGTH: 363 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GAATTCTGCA AATTTGGAAA CCTGTCCACT TACCTGAGGA CGAAGAGAAA TGAATTTGTC      60

CCCTACAAGA CCAAAGGGGC ACGATTCCGT CAAGGGAAAG ACTACGTTGG AGCAATCCCT     120

GTGGATCTGA AACGGCGCTT GGACACGCAT CACCAGTAGC CAGAGCTCAG CCAGCTCTGG     180

ATTTGTGGAG GAGAAGTCCC TCAGTGATGT AGAAGAAGAG GAAGCTCCTG AAGATCTGTA     240
```

```
TAAGGACTTC CTGACCTTGG AGCATCTCAT CTGTTACAGT TTCCAAGTGG CTAAGGGCAT      300

GGAGTTCTTG GCATCGCGAA AGTGTATCCA CAGAGACCTG GCAGCCAGGA ACGTGCTGAA      360

TTC                                                                   363
```

(2) INFORMATION FOR SEQ ID NO:4:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
GTCGACAATC TGTTGGGGGC CTGCACCATC CCAACATCCT GCTGCTCTAC AACTATTTTT      60

ATGACCGGAG GAGGATCTAC TTGATTCTAG AGTATGCCCC CCGCGGAGCT CTACAAGGAG     120

CTGCAGAAGA GCTGCACATT TGACGAGCAG CGAACAGCCA CGATCATGGA GGAGTTGGCA     180

GATGCTCTAA TGTACTGCCG TGGGAAGAAG GTGATTCACA GAGACCTGGC AGCCAGCAAC     240

GTGCTGAATT C                                                         251
```

(2) INFORMATION FOR SEQ ID NO:5:

(i) SEQUENCE CHARACTERISTICS:
        (A) LENGTH: 510 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:
        (A) AUTHORS: Gronwald, R., et al.
        (C) JOURNAL: Proc. Natl. Acad. Sci. U.S.A.
        (D) VOLUME: 85
        (F) PAGES: 3435-3439
        (G) DATE: 1988

(xi) SEQUENCE DESCRIPTION: SEQ ID NO:5:

```
AACCTGTGGG GGCCTGCACC AAAGGAGGAC CATCTATATC ATCTATATCA TCACTGAGTA      60

CTGCCGCTAC GGAGACCTGG TGGACTACCT GCACCGCAAC AAACACACCT TCCTGCAGCA     120

CCACTCCGAC AAGCGCCGCC CGCCCAGCGC GGAGCTCTAC AGCAATGCTC TGCCCGTTGG     180

GCTCCCCCTG CCCAGCCATG TGTCCTTGAC CGGGGGAGAG CGACGGTGGC TACATGGACA     240

TGAGCAAGGA CGAGTCGGTG GACTATGTGC CCATGCTGGA CATGAAAGGA GACGTCAAAT     300

AGCAGACATC GAGTCCTCCA ACTACATGGC CCCTTACGAT AACTACGTTC CCTCTGCCCC     360

TGAGAGGACC TGCCGAGCAA CTTTGATCAA CGAGTCTCCA GTGCTAAGCT ACATGGACCT     420

CGTGGGCTTC AGCTACCAGG TGGCCAATGG CATGGAGTTC TGGCCTCCAA GAACTGCGTC     480

CACAGAGACC TGGCGGCTAG GAACGTCCTT                                     510
```

(2) INFORMATION FOR SEQ ID NO:6:

(i) SEQUENCE CHARACTERISTICS:
        (A) LENGTH: 255 base pairs
        (B) TYPE: nucleic acid
        (C) STRANDEDNESS: single
        (D) TOPOLOGY: linear (ii) MOLECULE TYPE: DNA (genomic)

(x) PUBLICATION INFORMATION:

-continued (A) AUTHORS: Ruta, M., et al.
(C) JOURNAL: Oncogene
(D) VOLUME: 3
(F) PAGES: 9-15
(G) DATE: 1988

(x i) SEQUENCE DESCRIPTION: SEQ ID NO:6:

```
AACCTGCTGG GGGCCTGCAC GCAGGATGGT CCCTTGTATG TCATCGTGGA GTATGCCTCC      60
AAGGGCAACC TGCGGGAGTA CCTGCAGACC CGGAGGCCCC CAGGGCTGGA ATACTGCTAT     120
AACCCCAGCC ACAACCCAGA GGAGCAGCTC TCCTCCAAGG ACCTGGTGTC CTGCGCCTAC     180
CAGGAGGCCC GAGGCATGGA GTATCTGGCC TCCAAGAAGT GCATACACCG AGACCTGGCA     240
GCCAGGAATG TCCTG                                                      255
```

(2) INFORMATION FOR SEQ ID NO:7:

(i) SEQUENCE CHARACTERISTICS:
(A) LENGTH: 4236 base pairs
(B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 1..4068

(x i) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GAG | AGC | AAG | GTG | CTG | CTG | GCC | GTC | GCC | CTG | TGG | CTC | TGC | GTG | GAG | 48 |
| Met | Glu | Ser | Lys | Val | Leu | Leu | Ala | Val | Ala | Leu | Trp | Leu | Cys | Val | Glu | |
| 1 | | | | 5 | | | | | 10 | | | | | 15 | | |
| ACC | CGG | GCC | GCC | TCT | GTG | GGT | TTG | CCT | AGT | GTT | TCT | CTT | GAT | CTG | CCC | 96 |
| Thr | Arg | Ala | Ala | Ser | Val | Gly | Leu | Pro | Ser | Val | Ser | Leu | Asp | Leu | Pro | |
| | | | 20 | | | | | 25 | | | | | 30 | | | |
| AGG | CTC | AGC | ATA | CAA | AAA | GAC | ATA | CTT | ACA | ATT | AAG | GCT | AAT | ACA | ACT | 144 |
| Arg | Leu | Ser | Ile | Gln | Lys | Asp | Ile | Leu | Thr | Ile | Lys | Ala | Asn | Thr | Thr | |
| | | | 35 | | | | 40 | | | | | 45 | | | | |
| CTT | CAA | ATT | ACT | TGC | AGG | GGA | CAG | AGG | GAC | TTG | GAC | TGG | CTT | TGG | CCC | 192 |
| Leu | Gln | Ile | Thr | Cys | Arg | Gly | Gln | Arg | Asp | Leu | Asp | Trp | Leu | Trp | Pro | |
| | 50 | | | | | 55 | | | | | 60 | | | | | |
| AAT | AAT | CAG | AGT | GGC | AGT | GAG | CAA | AGG | GTG | GAG | GTG | ACT | GAG | TGC | AGC | 240 |
| Asn | Asn | Gln | Ser | Gly | Ser | Glu | Gln | Arg | Val | Glu | Val | Thr | Glu | Cys | Ser | |
| 65 | | | | | 70 | | | | | 75 | | | | | 80 | |
| GAT | GGC | CTC | TTC | TGT | AAG | ACA | CTC | ACA | ATT | CCA | AAA | GTG | ATC | GGA | AAT | 288 |
| Asp | Gly | Leu | Phe | Cys | Lys | Thr | Leu | Thr | Ile | Pro | Lys | Val | Ile | Gly | Asn | |
| | | | | 85 | | | | | 90 | | | | | 95 | | |
| GAC | ACT | GGA | GCC | TAC | AAG | TGC | TTC | TAC | CGG | GAA | ACT | GAC | TTG | GCC | TCG | 336 |
| Asp | Thr | Gly | Ala | Tyr | Lys | Cys | Phe | Tyr | Arg | Glu | Thr | Asp | Leu | Ala | Ser | |
| | | | 100 | | | | | 105 | | | | | 110 | | | |
| GTC | ATT | TAT | GTC | TAT | GTT | CAA | GAT | TAC | AGA | TCT | CCA | TTT | ATT | GCT | TCT | 384 |
| Val | Ile | Tyr | Val | Tyr | Val | Gln | Asp | Tyr | Arg | Ser | Pro | Phe | Ile | Ala | Ser | |
| | | | 115 | | | | | 120 | | | | | 125 | | | |
| GTT | AGT | GAC | CAA | CAT | GGA | GTC | GTG | TAC | ATT | ACT | GAG | AAC | AAA | AAC | AAA | 432 |
| Val | Ser | Asp | Gln | His | Gly | Val | Val | Tyr | Ile | Thr | Glu | Asn | Lys | Asn | Lys | |
| | | 130 | | | | | 135 | | | | | 140 | | | | |
| ACT | GTG | GTG | ATT | CCA | TGT | CTC | GGG | TCC | ATT | TCA | AAT | CTC | AAC | GTG | TCA | 480 |
| Thr | Val | Val | Ile | Pro | Cys | Leu | Gly | Ser | Ile | Ser | Asn | Leu | Asn | Val | Ser | |
| 145 | | | | | 150 | | | | | 155 | | | | | 160 | |
| CTT | TGT | GCA | AGA | TAC | CCA | GAA | AAG | AGA | TTT | GTT | CCT | GAT | GGT | AAC | AGA | 528 |
| Leu | Cys | Ala | Arg | Tyr | Pro | Glu | Lys | Arg | Phe | Val | Pro | Asp | Gly | Asn | Arg | |
| | | | | 165 | | | | | 170 | | | | | 175 | | |
| ATT | TCC | TGG | GAC | AGC | AAG | AAG | GGC | TTT | ACT | ATT | CCC | AGC | TAC | ATG | ATC | 576 |

|     |     |     |     |     |     |     |     |     |     |     |     |     |     |     |
|---|---|---|---|---|---|---|---|---|---|---|---|---|---|---|
| Ile | Ser | Trp | Asp<br>180 | Ser | Lys | Lys | Gly | Phe<br>185 | Thr | Ile | Pro | Ser | Tyr<br>190 | Met | Ile |

| AGC | TAT | GCT | GGC | ATG | GTC | TTC | TGT | GAA | GCA | AAA | ATT | AAT | GAT | GAA | AGT | 624 |
|---|---|---|---|---|---|---|---|---|---|---|---|---|---|---|---|---|
| Ser | Tyr | Ala<br>195 | Gly | Met | Val | Phe | Cys<br>200 | Glu | Ala | Lys | Ile | Asn<br>205 | Asp | Glu | Ser | |

| TAC | CAG | TCT | ATT | ATG | TAC | ATA | GTT | GTC | GTT | GTA | GGG | TAT | AGG | ATT | TAT | 672 |
|---|---|---|---|---|---|---|---|---|---|---|---|---|---|---|---|---|
| Tyr | Gln<br>210 | Ser | Ile | Met | Tyr | Ile<br>215 | Val | Val | Val | Val | Gly<br>220 | Tyr | Arg | Ile | Tyr | |

| GAT | GTG | GTT | CTG | AGT | CCG | TCT | CAT | GGA | ATT | GAA | CTA | TCT | GTT | GGA | GAA | 720 |
|---|---|---|---|---|---|---|---|---|---|---|---|---|---|---|---|---|
| Asp<br>225 | Val | Val | Leu | Ser | Pro<br>230 | Ser | His | Gly | Ile | Glu<br>235 | Leu | Ser | Val | Gly | Glu<br>240 | |

| AAG | CTT | GTC | TTA | AAT | TGT | ACA | GCA | AGA | ACT | GAA | CTA | AAT | GTG | GGG | ATT | 768 |
|---|---|---|---|---|---|---|---|---|---|---|---|---|---|---|---|---|
| Lys | Leu | Val | Leu | Asn<br>245 | Cys | Thr | Ala | Arg | Thr<br>250 | Glu | Leu | Asn | Val | Gly<br>255 | Ile | |

| GAC | TTC | AAC | TGG | GAA | TAC | CCT | TCT | TCG | AAG | CAT | CAG | CAT | AAG | AAA | CTT | 816 |
|---|---|---|---|---|---|---|---|---|---|---|---|---|---|---|---|---|
| Asp | Phe | Asn | Trp<br>260 | Glu | Tyr | Pro | Ser | Ser<br>265 | Lys | His | Gln | His | Lys<br>270 | Lys | Leu | |

| GTA | AAC | CGA | GAC | CTA | AAA | ACC | CAG | TCT | GGG | AGT | GAG | ATG | AAG | AAA | TTT | 864 |
|---|---|---|---|---|---|---|---|---|---|---|---|---|---|---|---|---|
| Val | Asn | Arg<br>275 | Asp | Leu | Lys | Thr | Gln<br>280 | Ser | Gly | Ser | Glu | Met<br>285 | Lys | Lys | Phe | |

| TTG | AGC | ACC | TTA | ACT | ATA | GAT | GGT | GTA | ACC | CGG | AGT | GAC | CAA | GGA | TTG | 912 |
|---|---|---|---|---|---|---|---|---|---|---|---|---|---|---|---|---|
| Leu | Ser | Thr<br>290 | Leu | Thr | Ile | Asp | Gly<br>295 | Val | Thr | Arg | Ser | Asp<br>300 | Gln | Gly | Leu | |

| TAC | ACC | TGT | GCA | GCA | TCC | AGT | GGG | CTG | ATG | ACC | AAG | AAG | AAC | AGC | ACA | 960 |
|---|---|---|---|---|---|---|---|---|---|---|---|---|---|---|---|---|
| Tyr | Thr<br>305 | Cys | Ala | Ala | Ser | Ser<br>310 | Gly | Leu | Met | Thr<br>315 | Lys | Lys | Asn | Ser | Thr<br>320 | |

| TTT | GTC | AGG | GTC | CAT | GAA | AAA | CCT | TTT | GTT | GCT | TTT | GGA | AGT | GGC | ATG | 1008 |
|---|---|---|---|---|---|---|---|---|---|---|---|---|---|---|---|---|
| Phe | Val | Arg | Val | His<br>325 | Glu | Lys | Pro | Phe | Val<br>330 | Ala | Phe | Gly | Ser | Gly<br>335 | Met | |

| GAA | TCT | CTG | GTG | GAA | GCC | ACG | GTG | GGG | GAG | CGT | GTC | AGA | ATC | CCT | GCG | 1056 |
|---|---|---|---|---|---|---|---|---|---|---|---|---|---|---|---|---|
| Glu | Ser | Leu | Val<br>340 | Glu | Ala | Thr | Val | Gly<br>345 | Glu | Arg | Val | Arg | Ile<br>350 | Pro | Ala | |

| AAG | TAC | CTT | GGT | TAC | CCA | CCC | CCA | GAA | ATA | AAA | TGG | TAT | AAA | AAT | GGA | 1104 |
|---|---|---|---|---|---|---|---|---|---|---|---|---|---|---|---|---|
| Lys | Tyr | Leu<br>355 | Gly | Tyr | Pro | Pro | Pro<br>360 | Glu | Ile | Lys | Trp | Tyr<br>365 | Lys | Asn | Gly | |

| ATA | CCC | CTT | GAG | TCC | AAT | CAC | ACA | ATT | AAA | GCG | GGG | CAT | GTA | CTG | ACG | 1152 |
|---|---|---|---|---|---|---|---|---|---|---|---|---|---|---|---|---|
| Ile | Pro | Leu<br>370 | Glu | Ser | Asn | His | Thr<br>375 | Ile | Lys | Ala | Gly | His<br>380 | Val | Leu | Thr | |

| ATT | ATG | GAA | GTG | AGT | GAA | AGA | GAC | ACA | GGA | AAT | TAC | ACT | GTC | ATC | CTT | 1200 |
|---|---|---|---|---|---|---|---|---|---|---|---|---|---|---|---|---|
| Ile<br>385 | Met | Glu | Val | Ser | Glu<br>390 | Arg | Asp | Thr | Gly | Asn<br>395 | Tyr | Thr | Val | Ile | Leu<br>400 | |

| ACC | AAT | CCC | ATT | TCA | AAG | GAG | AAG | CAG | AGC | CAT | GTG | GTC | TCT | CTG | GTT | 1248 |
|---|---|---|---|---|---|---|---|---|---|---|---|---|---|---|---|---|
| Thr | Asn | Pro | Ile | Ser<br>405 | Lys | Glu | Lys | Gln | Ser<br>410 | His | Val | Val | Ser | Leu<br>415 | Val | |

| GTG | TAT | GTC | CCA | CCC | CAG | ATT | GGT | GAG | AAA | TCT | CTA | ATC | TCT | CCT | GTG | 1296 |
|---|---|---|---|---|---|---|---|---|---|---|---|---|---|---|---|---|
| Val | Tyr | Val | Pro<br>420 | Pro | Gln | Ile | Gly | Glu<br>425 | Lys | Ser | Leu | Ile | Ser<br>430 | Pro | Val | |

| GAT | TCC | TAC | CAG | TAC | GGC | ACC | ACT | CAA | ACG | CTG | ACA | TGT | ACG | GTC | TAT | 1344 |
|---|---|---|---|---|---|---|---|---|---|---|---|---|---|---|---|---|
| Asp | Ser | Tyr<br>435 | Gln | Tyr | Gly | Thr | Thr<br>440 | Gln | Thr | Leu | Thr | Cys<br>445 | Thr | Val | Tyr | |

| GCC | ATT | CCT | CCC | CCG | CAT | CAC | ATC | CAC | TGG | TAT | TGG | CAG | TTG | GAG | GAA | 1392 |
|---|---|---|---|---|---|---|---|---|---|---|---|---|---|---|---|---|
| Ala | Ile | Pro<br>450 | Pro | Pro | His | His<br>455 | Ile | His | Trp | Tyr | Trp<br>460 | Gln | Leu | Glu | Glu | |

| GAG | TGC | GCC | AAC | GAG | CCC | AGC | CAA | GCT | GTC | TCA | GTG | ACA | AAC | CCA | TAC | 1440 |
|---|---|---|---|---|---|---|---|---|---|---|---|---|---|---|---|---|
| Glu<br>465 | Cys | Ala | Asn | Glu | Pro<br>470 | Ser | Gln | Ala | Val | Ser<br>475 | Val | Thr | Asn | Pro | Tyr<br>480 | |

| CCT | TGT | GAA | GAA | TGG | AGA | AGT | GTG | GAG | GAC | TTC | CAG | GGA | GGA | AAT | AAA | 1488 |
|---|---|---|---|---|---|---|---|---|---|---|---|---|---|---|---|---|
| Pro | Cys | Glu | Glu | Trp<br>485 | Arg | Ser | Val | Glu | Asp<br>490 | Phe | Gln | Gly | Gly | Asn<br>495 | Lys | |

| ATT | GAA | GTT | AAT | AAA | AAT | CAA | TTT | GCT | CTA | ATT | GAA | GGA | AAA | AAC | AAA | 1536 |
|---|---|---|---|---|---|---|---|---|---|---|---|---|---|---|---|---|

```
                Ile Glu Val Asn Lys Asn Gln Phe Ala Leu Ile Glu Gly Lys Asn Lys
                            500                 505                 510

ACT GTA AGT ACC CTT GTT ATC CAA GCG GCA AAT GTG TCA GCT TTG TAC            1584
Thr Val Ser Thr Leu Val Ile Gln Ala Ala Asn Val Ser Ala Leu Tyr
        515                 520                 525

AAA TGT GAA GCG GTC AAC AAA GTC GGG AGA GGA GAG AGG GTG ATC TCC            1632
Lys Cys Glu Ala Val Asn Lys Val Gly Arg Gly Glu Arg Val Ile Ser
530                 535                 540

TTC CAC GTG ACC AGG GGT CCT GAA ATT ACT TTG CAA CCT GAC ATG CAG            1680
Phe His Val Thr Arg Gly Pro Glu Ile Thr Leu Gln Pro Asp Met Gln
545                 550                 555                 560

CCC ACT GAG CAG GAG AGC GTG TCT TTG TGG TGC ACT GCA GAC AGA TCT            1728
Pro Thr Glu Gln Glu Ser Val Ser Leu Trp Cys Thr Ala Asp Arg Ser
                565                 570                 575

ACG TTT GAG AAC CTC ACA TGG TAC AAG CTT GGC CCA CAG CCT CTG CCA            1776
Thr Phe Glu Asn Leu Thr Trp Tyr Lys Leu Gly Pro Gln Pro Leu Pro
            580                 585                 590

ATC CAT GTG GGA GAG TTG CCC ACA CCT GTT TGC AAG AAC TTG GAT ACT            1824
Ile His Val Gly Glu Leu Pro Thr Pro Val Cys Lys Asn Leu Asp Thr
        595                 600                 605

CTT TGG AAA TTG AAT GCC ACC ATG TTC TCT AAT AGC ACA AAT GAC ATT            1872
Leu Trp Lys Leu Asn Ala Thr Met Phe Ser Asn Ser Thr Asn Asp Ile
610                 615                 620

TTG ATC ATG GAG CTT AAG AAT GCA TCC TTG CAG GAC CAA GGA GAC TAT            1920
Leu Ile Met Glu Leu Lys Asn Ala Ser Leu Gln Asp Gln Gly Asp Tyr
625                 630                 635                 640

GTC TGC CTT GCT CAA GAC AGG AAG ACC AAG AAA AGA CAT TGC GTG GTC            1968
Val Cys Leu Ala Gln Asp Arg Lys Thr Lys Lys Arg His Cys Val Val
                645                 650                 655

AGG CAG CTC ACA GTC CTA GAG CGT GTG GCA CCC ACG ATC ACA GGA AAC            2016
Arg Gln Leu Thr Val Leu Glu Arg Val Ala Pro Thr Ile Thr Gly Asn
            660                 665                 670

CTG GAG AAT CAG ACG ACA AGT ATT GGG GAA AGC ATC GAA GTC TCA TGC            2064
Leu Glu Asn Gln Thr Thr Ser Ile Gly Glu Ser Ile Glu Val Ser Cys
        675                 680                 685

ACG GCA TCT GGG AAT CCC CCT CCA CAG ATC ATG TGG TTT AAA GAT AAT            2112
Thr Ala Ser Gly Asn Pro Pro Pro Gln Ile Met Trp Phe Lys Asp Asn
690                 695                 700

GAG ACC CTT GTA GAA GAC TCA GGC ATT GTA TTG AAG GAT GGG AAC CGG            2160
Glu Thr Leu Val Glu Asp Ser Gly Ile Val Leu Lys Asp Gly Asn Arg
705                 710                 715                 720

AAC CTC ACT ATC CGC AGA GTG AGG AAG GAG GAC GAA GGC CTC TAC ACC            2208
Asn Leu Thr Ile Arg Arg Val Arg Lys Glu Asp Glu Gly Leu Tyr Thr
                725                 730                 735

TGC CAG GCA TGC AGT GTT CTT GGC TGT GCA AAA GTG GAG GCA TTT TTC            2256
Cys Gln Ala Cys Ser Val Leu Gly Cys Ala Lys Val Glu Ala Phe Phe
            740                 745                 750

ATA ATA GAA GGT GCC CAG GAA AAG ACG AAC TTG GAA ATC ATT ATT CTA            2304
Ile Ile Glu Gly Ala Gln Glu Lys Thr Asn Leu Glu Ile Ile Ile Leu
        755                 760                 765

GTA GGC ACG ACG GTG ATT GCC ATG TTC TTC TGG CTA CTT CTT GTC ATC            2352
Val Gly Thr Thr Val Ile Ala Met Phe Phe Trp Leu Leu Leu Val Ile
770                 775                 780

ATC CTA GGG ACC GTT AAG CGG GCC AAT GGA GGG GAA CTG AAG ACA GGC            2400
Ile Leu Gly Thr Val Lys Arg Ala Asn Gly Gly Glu Leu Lys Thr Gly
785                 790                 795                 800

TAC TTG TCC ATC GTC ATG GAT CCA GAT GAA CTC CCA TTG GAT GAA CAT            2448
Tyr Leu Ser Ile Val Met Asp Pro Asp Glu Leu Pro Leu Asp Glu His
                805                 810                 815

TGT GAA CGA CTG CCT TAT GAT GCC AGC AAA TGG GAA TTC CCC AGA GAC            2496
```

|  |  |  |  |  |  |  |  |  |  |  |  |  |  |  |  |
|---|---|---|---|---|---|---|---|---|---|---|---|---|---|---|---|
| Cys | Glu | Arg | Leu<br>820 | Pro | Tyr | Asp | Ala | Ser<br>825 | Lys | Trp | Glu | Phe | Pro<br>830 | Arg | Asp |

| CGG | CTG | AAC | CTA | GGT | AAG | CCT | CTT | GGC | CGT | GGT | GCC | TTT | GGC | CAA | GAG | 2544 |
|---|---|---|---|---|---|---|---|---|---|---|---|---|---|---|---|---|
| Arg | Leu | Asn | Leu | Gly | Lys | Pro | Leu | Gly | Arg | Gly | Ala | Phe | Gly | Gln | Glu |  |
|  |  | 835 |  |  |  | 840 |  |  |  |  | 845 |  |  |  |  |  |

| ATT | GAA | GCA | GAT | GCC | TTT | GGA | ATT | GAC | AAG | ACA | GCA | ACT | TGC | AGG | ACA | 2592 |
|---|---|---|---|---|---|---|---|---|---|---|---|---|---|---|---|---|
| Ile | Glu | Ala | Asp | Ala | Phe | Gly | Ile | Asp | Lys | Thr | Ala | Thr | Cys | Arg | Thr |  |
| 850 |  |  |  |  | 855 |  |  |  |  | 860 |  |  |  |  |  |  |

| GTA | GCA | GTC | AAA | ATG | TTG | AAA | GAA | GGA | GCA | ACA | CAC | AGT | GAG | CAT | CGA | 2640 |
|---|---|---|---|---|---|---|---|---|---|---|---|---|---|---|---|---|
| Val | Ala | Val | Lys | Met | Leu | Lys | Glu | Gly | Ala | Thr | His | Ser | Glu | His | Arg |  |
| 865 |  |  |  |  | 870 |  |  |  |  | 875 |  |  |  |  | 880 |  |

| GCT | CTC | ATG | TCT | GAA | CTC | AAG | ATC | CTC | ATT | CAT | ATT | GGT | CAC | CAT | CTC | 2688 |
|---|---|---|---|---|---|---|---|---|---|---|---|---|---|---|---|---|
| Ala | Leu | Met | Ser | Glu | Leu | Lys | Ile | Leu | Ile | His | Ile | Gly | His | His | Leu |  |
|  |  |  |  | 885 |  |  |  |  | 890 |  |  |  |  | 895 |  |  |

| AAT | GTG | GTC | AAC | CTT | CTA | GGT | GCC | TGT | ACC | AAG | CCA | GGA | GGG | CCA | CTC | 2736 |
|---|---|---|---|---|---|---|---|---|---|---|---|---|---|---|---|---|
| Asn | Val | Val | Asn | Leu | Leu | Gly | Ala | Cys | Thr | Lys | Pro | Gly | Gly | Pro | Leu |  |
|  |  |  | 900 |  |  |  |  | 905 |  |  |  |  | 910 |  |  |  |

| ATG | GTG | ATT | GTG | GAA | TTC | TGC | AAA | TTT | GGA | AAC | CTG | TCC | ACT | TAC | CTG | 2784 |
|---|---|---|---|---|---|---|---|---|---|---|---|---|---|---|---|---|
| Met | Val | Ile | Val | Glu | Phe | Cys | Lys | Phe | Gly | Asn | Leu | Ser | Thr | Tyr | Leu |  |
|  |  | 915 |  |  |  |  | 920 |  |  |  |  | 925 |  |  |  |  |

| AGG | AGC | AAG | AGA | AAT | GAA | TTT | GTC | CCC | TAC | AAG | ACC | AAA | GGG | GCA | CGA | 2832 |
|---|---|---|---|---|---|---|---|---|---|---|---|---|---|---|---|---|
| Arg | Ser | Lys | Arg | Asn | Glu | Phe | Val | Pro | Tyr | Lys | Thr | Lys | Gly | Ala | Arg |  |
|  | 930 |  |  |  |  | 935 |  |  |  |  | 940 |  |  |  |  |  |

| TTC | CGT | CAA | GGG | AAA | GAC | TAC | GTT | GGA | GCA | ATC | CCT | GTG | GAT | CTG | AAA | 2880 |
|---|---|---|---|---|---|---|---|---|---|---|---|---|---|---|---|---|
| Phe | Arg | Gln | Gly | Lys | Asp | Tyr | Val | Gly | Ala | Ile | Pro | Val | Asp | Leu | Lys |  |
| 945 |  |  |  |  | 950 |  |  |  |  | 955 |  |  |  |  | 960 |  |

| CGG | CGC | TTG | GAC | AGC | ATC | ACC | AGT | AGC | CAG | AGC | TCA | GCC | AGC | TCT | GGA | 2928 |
|---|---|---|---|---|---|---|---|---|---|---|---|---|---|---|---|---|
| Arg | Arg | Leu | Asp | Ser | Ile | Thr | Ser | Ser | Gln | Ser | Ser | Ala | Ser | Ser | Gly |  |
|  |  |  |  | 965 |  |  |  |  | 970 |  |  |  |  | 975 |  |  |

| TTT | GTG | GAG | GAG | AAG | TCC | CTC | AGT | GAT | GTA | GAA | GAA | GAG | GAA | GCT | CCT | 2976 |
|---|---|---|---|---|---|---|---|---|---|---|---|---|---|---|---|---|
| Phe | Val | Glu | Glu | Lys | Ser | Leu | Ser | Asp | Val | Glu | Glu | Glu | Glu | Ala | Pro |  |
|  |  |  | 980 |  |  |  |  | 985 |  |  |  |  | 990 |  |  |  |

| GAA | GAT | CTG | TAT | AAG | GAC | TTC | CTG | ACC | TTG | GAG | CAT | CTC | ATC | TGT | TAC | 3024 |
|---|---|---|---|---|---|---|---|---|---|---|---|---|---|---|---|---|
| Glu | Asp | Leu | Tyr | Lys | Asp | Phe | Leu | Thr | Leu | Glu | His | Leu | Ile | Cys | Tyr |  |
|  |  |  | 995 |  |  |  |  | 1000 |  |  |  |  | 1005 |  |  |  |

| AGC | TTC | CAA | GTG | GCT | AAG | GGC | ATG | GAG | TTC | TTG | GCA | TCG | CGA | AAG | TGT | 3072 |
|---|---|---|---|---|---|---|---|---|---|---|---|---|---|---|---|---|
| Ser | Phe | Gln | Val | Ala | Lys | Gly | Met | Glu | Phe | Leu | Ala | Ser | Arg | Lys | Cys |  |
|  |  | 1010 |  |  |  |  | 1015 |  |  |  |  | 1020 |  |  |  |  |

| ATC | CAC | AGG | GAC | CTG | GCG | GCA | CGA | AAT | ATC | CTC | TTA | TCG | GAG | AAG | AAC | 3120 |
|---|---|---|---|---|---|---|---|---|---|---|---|---|---|---|---|---|
| Ile | His | Arg | Asp | Leu | Ala | Ala | Arg | Asn | Ile | Leu | Leu | Ser | Glu | Lys | Asn |  |
| 1025 |  |  |  | 1030 |  |  |  |  | 1035 |  |  |  |  | 1040 |  |  |

| GTG | GTT | AAA | ATC | TGT | GAC | TTT | GGC | TTG | GCC | CGG | GAT | ATT | TAT | AAA | GAT | 3168 |
|---|---|---|---|---|---|---|---|---|---|---|---|---|---|---|---|---|
| Val | Val | Lys | Ile | Cys | Asp | Phe | Gly | Leu | Ala | Arg | Asp | Ile | Tyr | Lys | Asp |  |
|  |  |  | 1045 |  |  |  |  | 1050 |  |  |  |  | 1055 |  |  |  |

| CCA | GAT | TAT | GTC | AGA | AAA | GGA | GAT | GCT | CGC | CTC | CCT | TTG | AAA | TGG | ATG | 3216 |
|---|---|---|---|---|---|---|---|---|---|---|---|---|---|---|---|---|
| Pro | Asp | Tyr | Val | Arg | Lys | Gly | Asp | Ala | Arg | Leu | Pro | Leu | Lys | Trp | Met |  |
|  |  |  | 1060 |  |  |  |  | 1065 |  |  |  |  | 1070 |  |  |  |

| GCC | CCA | GAA | ACA | ATT | TTT | GAC | AGA | GTG | TAC | ACA | ATC | CAG | AGT | GAC | GTC | 3264 |
|---|---|---|---|---|---|---|---|---|---|---|---|---|---|---|---|---|
| Ala | Pro | Glu | Thr | Ile | Phe | Asp | Arg | Val | Tyr | Thr | Ile | Gln | Ser | Asp | Val |  |
|  |  |  | 1075 |  |  |  |  | 1080 |  |  |  |  | 1085 |  |  |  |

| TGG | TCT | TTT | GGT | GTT | TTG | CTG | TGG | GAA | ATA | TTT | TCC | TTA | GGT | GCT | TCT | 3312 |
|---|---|---|---|---|---|---|---|---|---|---|---|---|---|---|---|---|
| Trp | Ser | Phe | Gly | Val | Leu | Leu | Trp | Glu | Ile | Phe | Ser | Leu | Gly | Ala | Ser |  |
|  |  | 1090 |  |  |  |  | 1095 |  |  |  |  | 1100 |  |  |  |  |

| CCA | TAT | CCT | GGG | GTA | AAG | ATT | GAT | GAA | GAA | TTT | TGT | AGG | CGA | TTG | AAA | 3360 |
|---|---|---|---|---|---|---|---|---|---|---|---|---|---|---|---|---|
| Pro | Tyr | Pro | Gly | Val | Lys | Ile | Asp | Glu | Glu | Phe | Cys | Arg | Arg | Leu | Lys |  |
| 1105 |  |  |  |  | 1110 |  |  |  |  | 1115 |  |  |  |  | 1120 |  |

| GAA | GGA | ACT | AGA | ATG | AGG | GCC | CCT | GAT | TAT | ACT | ACA | CCA | GAA | ATG | TAC | 3408 |
|---|---|---|---|---|---|---|---|---|---|---|---|---|---|---|---|---|
| Glu | Gly | Thr | Arg | Met | Arg | Ala | Pro | Asp | Tyr | Thr | Thr | Pro | Glu | Met | Tyr |  |
|  |  |  | 1125 |  |  |  |  | 1130 |  |  |  |  | 1135 |  |  |  |

| CAG | ACC | ATG | CTG | GAC | TGC | TGG | CAC | GGG | GAG | CCC | AGT | CAG | AGA | CCC | ACG | 3456 |

| | | | | | | | | | | | | | | | |
|---|---|---|---|---|---|---|---|---|---|---|---|---|---|---|---|
|Gln|Thr|Met|Leu|Asp|Cys|Trp|His|Gly|Glu|Pro|Ser|Gln|Arg|Pro|Thr|
| | |1140| | | | |1145| | | |1150| | | | |

```
TTT TCA GAG TTG GTG GAA CAT TTG GGA AAT CTC TTG CAA GCT AAT GCT      3504
Phe Ser Glu Leu Val Glu His Leu Gly Asn Leu Leu Gln Ala Asn Ala
        1155                1160                1165

CAG CAG GAT GGC AAA GAC TAC ATT GTT CTT CCG ATA TCA GAG ACT TTG      3552
Gln Gln Asp Gly Lys Asp Tyr Ile Val Leu Pro Ile Ser Glu Thr Leu
    1170                1175                1180

AGC ATG GAA GAG GAT TCT GGA CTC TCT CTG CCT ACC TCA CCT GTT TCC      3600
Ser Met Glu Glu Asp Ser Gly Leu Ser Leu Pro Thr Ser Pro Val Ser
1185                1190                1195                1200

TGT ATG GAG GAG GAG GAA GTA TGT GAC CCC AAA TTC CAT TAT GAC AAC      3648
Cys Met Glu Glu Glu Glu Val Cys Asp Pro Lys Phe His Tyr Asp Asn
                1205                1210                1215

ACA GCA GGA ATC AGT CAG TAT CTG CAG AAC AGT AAG CGA AAG AGC CGG      3696
Thr Ala Gly Ile Ser Gln Tyr Leu Gln Asn Ser Lys Arg Lys Ser Arg
            1220                1225                1230

CCT GTG AGT GTA AAA ACA TTT GAA GAT ATC CCG TTA GAA GAA CCA GAA      3744
Pro Val Ser Val Lys Thr Phe Glu Asp Ile Pro Leu Glu Glu Pro Glu
        1235                1240                1245

GTA AAA GTA ATC CCA GAT GAC AAC CAG ACG GAC AGT GGT ATG GTT CTT      3792
Val Lys Val Ile Pro Asp Asp Asn Gln Thr Asp Ser Gly Met Val Leu
    1250                1255                1260

GCC TCA GAA GAG CTG AAA ACT TTG GAA GAC AGA ACC AAA TTA TCT CCA      3840
Ala Ser Glu Glu Leu Lys Thr Leu Glu Asp Arg Thr Lys Leu Ser Pro
1265                1270                1275                1280

TCT TTT GGT GGA ATG GTG CCC AGC AAA AGC AGG GAG TCT GTG GCA TCT      3888
Ser Phe Gly Gly Met Val Pro Ser Lys Ser Arg Glu Ser Val Ala Ser
                1285                1290                1295

GAA GGC TCA AAC CAG ACA AGC GGC TAC CAG TCC GGA TAT CAC TCC GAT      3936
Glu Gly Ser Asn Gln Thr Ser Gly Tyr Gln Ser Gly Tyr His Ser Asp
            1300                1305                1310

GAC ACA GAC ACC ACC GTG TAC TCC AGT GAG GAA GCA GAA CTT TTA AAG      3984
Asp Thr Asp Thr Thr Val Tyr Ser Ser Glu Glu Ala Glu Leu Leu Lys
        1315                1320                1325

CTG ATA GAG ATT GGA GTG CAA ACC GGT AGC ACA GCC CAG ATT CTC CAG      4032
Leu Ile Glu Ile Gly Val Gln Thr Gly Ser Thr Ala Gln Ile Leu Gln
    1330                1335                1340

CCT GAC ACG GGG ACC ACA CTG AGC TCT CCT CCT GTT TAAAAGGAAG           4078
Pro Asp Thr Gly Thr Thr Leu Ser Ser Pro Pro Val
1345                1350                1355

CATCCACACC CCAACTCCCG GACATCACAT GAGAGGTCTG CTCAGATTTT GAAGTGTTGT    4138

TCTTTCCACC AGCAGGAAGT AGCCGCATTT GATTTTCATT TCGACAACAG AAAAAGGACC    4198

TCGGACTGCA GGGAGCCAGC TCTTCTAGGC TTGTGACC                            4236
```

( 2 ) INFORMATION FOR SEQ ID NO:8:

( i ) SEQUENCE CHARACTERISTICS:
        ( A ) LENGTH: 1356 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met Glu Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
```

```
                    35                              40                              45

Leu  Gln  Ile  Thr  Cys  Arg  Gly  Gln  Arg  Asp  Leu  Asp  Trp  Leu  Trp  Pro
     50                        55                       60

Asn  Asn  Gln  Ser  Gly  Ser  Glu  Gln  Arg  Val  Glu  Val  Thr  Glu  Cys  Ser
65                            70                       75                       80

Asp  Gly  Leu  Phe  Cys  Lys  Thr  Leu  Thr  Ile  Pro  Lys  Val  Ile  Gly  Asn
                    85                            90                       95

Asp  Thr  Gly  Ala  Tyr  Lys  Cys  Phe  Tyr  Arg  Glu  Thr  Asp  Leu  Ala  Ser
               100                      105                 110

Val  Ile  Tyr  Val  Tyr  Val  Gln  Asp  Tyr  Arg  Ser  Pro  Phe  Ile  Ala  Ser
          115                      120                 125

Val  Ser  Asp  Gln  His  Gly  Val  Val  Tyr  Ile  Thr  Glu  Asn  Lys  Asn  Lys
     130                      135                 140

Thr  Val  Val  Ile  Pro  Cys  Leu  Gly  Ser  Ile  Ser  Asn  Leu  Asn  Val  Ser
145                      150                 155                           160

Leu  Cys  Ala  Arg  Tyr  Pro  Glu  Lys  Arg  Phe  Val  Pro  Asp  Gly  Asn  Arg
               165                      170                 175

Ile  Ser  Trp  Asp  Ser  Lys  Lys  Gly  Phe  Thr  Ile  Pro  Ser  Tyr  Met  Ile
               180                      185                 190

Ser  Tyr  Ala  Gly  Met  Val  Phe  Cys  Glu  Ala  Lys  Ile  Asn  Asp  Glu  Ser
               195                      200                 205

Tyr  Gln  Ser  Ile  Met  Tyr  Ile  Val  Val  Val  Gly  Tyr  Arg  Ile  Tyr
     210                      215                 220

Asp  Val  Val  Leu  Ser  Pro  Ser  His  Gly  Ile  Glu  Leu  Ser  Val  Gly  Glu
225                      230                 235                           240

Lys  Leu  Val  Leu  Asn  Cys  Thr  Ala  Arg  Thr  Glu  Leu  Asn  Val  Gly  Ile
                    245                      250                           255

Asp  Phe  Asn  Trp  Glu  Tyr  Pro  Ser  Ser  Lys  His  Gln  His  Lys  Lys  Leu
               260                      265                 270

Val  Asn  Arg  Asp  Leu  Lys  Thr  Gln  Ser  Gly  Ser  Glu  Met  Lys  Lys  Phe
          275                      280                 285

Leu  Ser  Thr  Leu  Thr  Ile  Asp  Gly  Val  Thr  Arg  Ser  Asp  Gln  Gly  Leu
     290                      295                 300

Tyr  Thr  Cys  Ala  Ala  Ser  Ser  Gly  Leu  Met  Thr  Lys  Lys  Asn  Ser  Thr
305                      310                 315                           320

Phe  Val  Arg  Val  His  Glu  Lys  Pro  Phe  Val  Ala  Phe  Gly  Ser  Gly  Met
               325                      330                 335

Glu  Ser  Leu  Val  Glu  Ala  Thr  Val  Gly  Glu  Arg  Val  Arg  Ile  Pro  Ala
               340                      345                 350

Lys  Tyr  Leu  Gly  Tyr  Pro  Pro  Pro  Glu  Ile  Lys  Trp  Tyr  Lys  Asn  Gly
               355                      360                 365

Ile  Pro  Leu  Glu  Ser  Asn  His  Thr  Ile  Lys  Ala  Gly  His  Val  Leu  Thr
     370                      375                 380

Ile  Met  Glu  Val  Ser  Glu  Arg  Asp  Thr  Gly  Asn  Tyr  Thr  Val  Ile  Leu
385                      390                 395                           400

Thr  Asn  Pro  Ile  Ser  Lys  Glu  Lys  Gln  Ser  His  Val  Val  Ser  Leu  Val
                    405                      410                 415

Val  Tyr  Val  Pro  Pro  Gln  Ile  Gly  Glu  Lys  Ser  Leu  Ile  Ser  Pro  Val
               420                      425                 430

Asp  Ser  Tyr  Gln  Tyr  Gly  Thr  Thr  Gln  Thr  Leu  Thr  Cys  Thr  Val  Tyr
               435                      440                 445

Ala  Ile  Pro  Pro  Pro  His  His  Ile  His  Trp  Tyr  Trp  Gln  Leu  Glu  Glu
               450                      455                 460
```

| | | | | | | | | | | | | | | |
|---|---|---|---|---|---|---|---|---|---|---|---|---|---|---|
| Glu | Cys | Ala | Asn | Glu | Pro | Ser | Gln | Ala | Val | Ser | Val | Thr | Asn | Pro | Tyr |
| 465 | | | | 470 | | | | 475 | | | | | | 480 |
| Pro | Cys | Glu | Glu | Trp | Arg | Ser | Val | Glu | Asp | Phe | Gln | Gly | Gly | Asn | Lys |
| | | | | 485 | | | | 490 | | | | | 495 | | |
| Ile | Glu | Val | Asn | Lys | Asn | Gln | Phe | Ala | Leu | Ile | Glu | Gly | Lys | Asn | Lys |
| | | | 500 | | | | | 505 | | | | | 510 | | |
| Thr | Val | Ser | Thr | Leu | Val | Ile | Gln | Ala | Ala | Asn | Val | Ser | Ala | Leu | Tyr |
| | | 515 | | | | | 520 | | | | | 525 | | | |
| Lys | Cys | Glu | Ala | Val | Asn | Lys | Val | Gly | Arg | Gly | Glu | Arg | Val | Ile | Ser |
| | 530 | | | | | 535 | | | | | 540 | | | | |
| Phe | His | Val | Thr | Arg | Gly | Pro | Glu | Ile | Thr | Leu | Gln | Pro | Asp | Met | Gln |
| 545 | | | | | 550 | | | | | 555 | | | | | 560 |
| Pro | Thr | Glu | Gln | Glu | Ser | Val | Ser | Leu | Trp | Cys | Thr | Ala | Asp | Arg | Ser |
| | | | | | 565 | | | | | 570 | | | | 575 | |
| Thr | Phe | Glu | Asn | Leu | Thr | Trp | Tyr | Lys | Leu | Gly | Pro | Gln | Pro | Leu | Pro |
| | | | 580 | | | | | 585 | | | | | 590 | | |
| Ile | His | Val | Gly | Glu | Leu | Pro | Thr | Pro | Val | Cys | Lys | Asn | Leu | Asp | Thr |
| | | 595 | | | | | 600 | | | | | 605 | | | |
| Leu | Trp | Lys | Leu | Asn | Ala | Thr | Met | Phe | Ser | Asn | Ser | Thr | Asn | Asp | Ile |
| | 610 | | | | | 615 | | | | | 620 | | | | |
| Leu | Ile | Met | Glu | Leu | Lys | Asn | Ala | Ser | Leu | Gln | Asp | Gln | Gly | Asp | Tyr |
| 625 | | | | | 630 | | | | | 635 | | | | | 640 |
| Val | Cys | Leu | Ala | Gln | Asp | Arg | Lys | Thr | Lys | Lys | Arg | His | Cys | Val | Val |
| | | | | 645 | | | | | 650 | | | | | 655 | |
| Arg | Gln | Leu | Thr | Val | Leu | Glu | Arg | Val | Ala | Pro | Thr | Ile | Thr | Gly | Asn |
| | | | 660 | | | | | 665 | | | | | 670 | | |
| Leu | Glu | Asn | Gln | Thr | Thr | Ser | Ile | Gly | Glu | Ser | Ile | Glu | Val | Ser | Cys |
| | | | 675 | | | | | 680 | | | | | 685 | | |
| Thr | Ala | Ser | Gly | Asn | Pro | Pro | Pro | Gln | Ile | Met | Trp | Phe | Lys | Asp | Asn |
| | 690 | | | | | 695 | | | | | 700 | | | | |
| Glu | Thr | Leu | Val | Glu | Asp | Ser | Gly | Ile | Val | Leu | Lys | Asp | Gly | Asn | Arg |
| 705 | | | | | 710 | | | | | 715 | | | | | 720 |
| Asn | Leu | Thr | Ile | Arg | Arg | Val | Arg | Lys | Glu | Asp | Glu | Gly | Leu | Tyr | Thr |
| | | | | 725 | | | | | 730 | | | | | 735 | |
| Cys | Gln | Ala | Cys | Ser | Val | Leu | Gly | Cys | Ala | Lys | Val | Glu | Ala | Phe | Phe |
| | | | 740 | | | | | 745 | | | | | 750 | | |
| Ile | Ile | Glu | Gly | Ala | Gln | Glu | Lys | Thr | Asn | Leu | Glu | Ile | Ile | Ile | Leu |
| | | 755 | | | | | 760 | | | | | 765 | | | |
| Val | Gly | Thr | Thr | Val | Ile | Ala | Met | Phe | Phe | Trp | Leu | Leu | Leu | Val | Ile |
| | 770 | | | | | 775 | | | | | 780 | | | | |
| Ile | Leu | Gly | Thr | Val | Lys | Arg | Ala | Asn | Gly | Gly | Glu | Leu | Lys | Thr | Gly |
| 785 | | | | | 790 | | | | | 795 | | | | | 800 |
| Tyr | Leu | Ser | Ile | Val | Met | Asp | Pro | Asp | Glu | Leu | Pro | Leu | Asp | Glu | His |
| | | | | 805 | | | | | 810 | | | | | 815 | |
| Cys | Glu | Arg | Leu | Pro | Tyr | Asp | Ala | Ser | Lys | Trp | Glu | Phe | Pro | Arg | Asp |
| | | | 820 | | | | | 825 | | | | | 830 | | |
| Arg | Leu | Asn | Leu | Gly | Lys | Pro | Leu | Gly | Arg | Gly | Ala | Phe | Gly | Gln | Glu |
| | | 835 | | | | | 840 | | | | | 845 | | | |
| Ile | Glu | Ala | Asp | Ala | Phe | Gly | Ile | Asp | Lys | Thr | Ala | Thr | Cys | Arg | Thr |
| | 850 | | | | | 855 | | | | | 860 | | | | |
| Val | Ala | Val | Lys | Met | Leu | Lys | Glu | Gly | Ala | Thr | His | Ser | Glu | His | Arg |
| 865 | | | | | 870 | | | | | 875 | | | | | 880 |
| Ala | Leu | Met | Ser | Glu | Leu | Lys | Ile | Leu | Ile | His | Ile | Gly | His | His | Leu |
| | | | | 885 | | | | | 890 | | | | | 895 | |

| | | | | | | | | | | | | | |
|---|---|---|---|---|---|---|---|---|---|---|---|---|---|
|Asn|Val|Val|Asn|Leu|Leu|Gly|Ala|Cys|Thr|Lys|Pro|Gly|Gly|Pro|Leu
| | | |900| | | |905| | | |910| | |
|Met|Val|Ile|Val|Glu|Phe|Cys|Lys|Phe|Gly|Asn|Leu|Ser|Thr|Tyr|Leu
| | |915| | | |920| | | |925| | | |
|Arg|Ser|Lys|Arg|Asn|Glu|Phe|Val|Pro|Tyr|Lys|Thr|Lys|Gly|Ala|Arg
| |930| | | |935| | | |940| | | | |
|Phe|Arg|Gln|Gly|Lys|Asp|Tyr|Val|Gly|Ala|Ile|Pro|Val|Asp|Leu|Lys
|945| | | |950| | | |955| | | | | |960

Reproducing as continuous text for clarity:

Asn Val Val Asn Leu Leu Gly Ala Cys Thr Lys Pro Gly Gly Pro Leu
                    900             905             910
Met Val Ile Val Glu Phe Cys Lys Phe Gly Asn Leu Ser Thr Tyr Leu
            915             920             925
Arg Ser Lys Arg Asn Glu Phe Val Pro Tyr Lys Thr Lys Gly Ala Arg
        930             935             940
Phe Arg Gln Gly Lys Asp Tyr Val Gly Ala Ile Pro Val Asp Leu Lys
945                 950             955                     960
Arg Arg Leu Asp Ser Ile Thr Ser Ser Gln Ser Ser Ala Ser Ser Gly
                965             970             975
Phe Val Glu Glu Lys Ser Leu Ser Asp Val Glu Glu Glu Ala Pro
            980             985             990
Glu Asp Leu Tyr Lys Asp Phe Leu Thr Leu Glu His Leu Ile Cys Tyr
            995             1000            1005
Ser Phe Gln Val Ala Lys Gly Met Glu Phe Leu Ala Ser Arg Lys Cys
        1010            1015            1020
Ile His Arg Asp Leu Ala Ala Arg Asn Ile Leu Leu Ser Glu Lys Asn
1025            1030            1035                    1040
Val Val Lys Ile Cys Asp Phe Gly Leu Ala Arg Asp Ile Tyr Lys Asp
                1045            1050            1055
Pro Asp Tyr Val Arg Lys Gly Asp Ala Arg Leu Pro Leu Lys Trp Met
            1060            1065            1070
Ala Pro Glu Thr Ile Phe Asp Arg Val Tyr Thr Ile Gln Ser Asp Val
        1075            1080            1085
Trp Ser Phe Gly Val Leu Leu Trp Glu Ile Phe Ser Leu Gly Ala Ser
    1090            1095            1100
Pro Tyr Pro Gly Val Lys Ile Asp Glu Glu Phe Cys Arg Arg Leu Lys
1105            1110            1115                    1120
Glu Gly Thr Arg Met Arg Ala Pro Asp Tyr Thr Thr Pro Glu Met Tyr
            1125            1130            1135
Gln Thr Met Leu Asp Cys Trp His Gly Glu Pro Ser Gln Arg Pro Thr
            1140            1145            1150
Phe Ser Glu Leu Val Glu His Leu Gly Asn Leu Leu Gln Ala Asn Ala
        1155            1160            1165
Gln Gln Asp Gly Lys Asp Tyr Ile Val Leu Pro Ile Ser Glu Thr Leu
        1170            1175            1180
Ser Met Glu Glu Asp Ser Gly Leu Ser Leu Pro Thr Ser Pro Val Ser
1185            1190            1195                    1200
Cys Met Glu Glu Glu Glu Val Cys Asp Pro Lys Phe His Tyr Asp Asn
            1205            1210            1215
Thr Ala Gly Ile Ser Gln Tyr Leu Gln Asn Ser Lys Arg Lys Ser Arg
            1220            1225            1230
Pro Val Ser Val Lys Thr Phe Glu Asp Ile Pro Leu Glu Glu Pro Glu
        1235            1240            1245
Val Lys Val Ile Pro Asp Asp Asn Gln Thr Asp Ser Gly Met Val Leu
1250                1255            1260
Ala Ser Glu Glu Leu Lys Thr Leu Glu Asp Arg Thr Lys Leu Ser Pro
1265            1270            1275                    1280
Ser Phe Gly Gly Met Val Pro Ser Lys Ser Arg Glu Ser Val Ala Ser
            1285            1290            1295
Glu Gly Ser Asn Gln Thr Ser Gly Tyr Gln Ser Gly Tyr His Ser Asp
            1300            1305            1310
Asp Thr Asp Thr Thr Val Tyr Ser Ser Glu Glu Ala Glu Leu Leu Lys

```
                   1315                       1320                          1325
Leu  Ile  Glu  Ile  Gly  Val  Gln  Thr  Gly  Ser  Thr  Ala  Gln  Ile  Leu  Gln
                 1330                      1335                 1340

Pro  Asp  Thr  Gly  Thr  Thr  Leu  Ser  Ser  Pro  Pro  Val
1345                      1350                     1355
```

(2) INFORMATION FOR SEQ ID NO:9:

(i) SEQUENCE CHARACTERISTICS:
        (A) LENGTH: 433 amino acids
        (B) TYPE: amino acid
        (D) TOPOLOGY: linear (ii) MOLECULE TYPE: peptide (x) PUBLICATION INFORMATION:
        (A) AUTHORS: Yarden, Y., et al.
        (C) JOURNAL: EMBO J.
        (D) VOLUME: 6
        (F) PAGES: 3341-3351
        (G) DATE: 1987

(xi) SEQUENCE DESCRIPTION: SEQ ID NO:9:

```
Leu  Thr  Tyr  Lys  Tyr  Leu  Gln  Lys  Pro  Met  Tyr  Glu  Val  Gln  Trp  Lys
1                   5                        10                       15

Val  Val  Glu  Glu  Ile  Asn  Gly  Asn  Asn  Tyr  Val  Tyr  Ile  Asp  Pro  Thr
                 20                       25                       30

Gln  Leu  Pro  Tyr  Asp  His  Lys  Trp  Glu  Phe  Pro  Arg  Asn  Arg  Leu  Ser
                 35                       40                       45

Phe  Gly  Lys  Thr  Leu  Gly  Ala  Gly  Ala  Phe  Gly  Lys  Val  Val  Ala  Glu
                 50                       55                       60

Thr  Ala  Tyr  Gly  Leu  Ile  Lys  Ser  Asp  Ala  Ala  Met  Thr  Val  Ala  Val
65                           70                       75                       80

Lys  Met  Leu  Lys  Pro  Ser  Ala  His  Leu  Thr  Glu  Arg  Glu  Ala  Leu  Met
                 85                       90                       95

Ser  Glu  Leu  Lys  Val  Leu  Ser  Tyr  Leu  Gly  Asn  His  Met  Asn  Ile  Val
                 100                      105                      110

Asn  Leu  Leu  Gly  Ala  Cys  Thr  Ile  Gly  Gly  Pro  Thr  Leu  Val  Ile  Thr
                 115                      120                      125

Glu  Tyr  Cys  Cys  Tyr  Gly  Asp  Leu  Leu  Asn  Phe  Leu  Arg  Arg  Lys  Arg
130                          135                      140

Asp  Ser  Phe  Ile  Cys  Ser  Lys  Gln  Glu  Asp  His  Ala  Glu  Ala  Ala  Leu
145                          150                      155                      160

Tyr  Lys  Asn  Leu  Leu  His  Ser  Lys  Glu  Ser  Ser  Cys  Ser  Asp  Ser  Thr
                 165                      170                      175

Asn  Glu  Tyr  Met  Asp  Met  Lys  Pro  Gly  Val  Ser  Tyr  Val  Val  Pro  Thr
                 180                      185                      190

Lys  Ala  Asp  Lys  Arg  Arg  Ser  Val  Arg  Ile  Gly  Ser  Tyr  Ile  Glu  Arg
                 195                      200                      205

Asp  Val  Thr  Pro  Ala  Ile  Met  Glu  Asp  Asp  Glu  Leu  Ala  Leu  Asp  Leu
                 210                      215                      220

Glu  Asp  Leu  Leu  Ser  Phe  Ser  Tyr  Gln  Val  Lys  Gly  Met  Ala  Phe  Leu
225                          230                      235                      240

Ala  Ser  Lys  Asn  Cys  Ile  His  Arg  Asp  Leu  Ala  Ala  Arg  Asn  Ile  Leu
                 245                      250                      255

Leu  Thr  His  Gly  Arg  Ile  Thr  Lys  Ile  Cys  Asp  Phe  Gly  Leu  Ala  Arg
                 260                      265                      270

Asp  Ile  Lys  Asn  Asp  Ser  Asn  Tyr  Val  Val  Lys  Gly  Asn  Ala  Arg  Leu
                 275                      280                      285
```

| | | | | | | | | | | | | | | | |
|---|---|---|---|---|---|---|---|---|---|---|---|---|---|---|---|
|Pro|Val|Lys|Val|Met|Ala|Pro|Glu|Ser|Ile|Phe|Asn|Cys|Val|Tyr|Thr|
| |290| | | |295| | | |300| | | | | | |
|Glu|Glu|Ser|Asp|Val|Trp|Ser|Tyr|Gly|Ile|Phe|Leu|Trp|Glu|Leu|Phe|
|305| | | | |310| | | |315| | | | | |320|
|Ser|Leu|Gly|Ser|Ser|Pro|Tyr|Pro|Gly|Met|Pro|Val|Lys|Ser|Lys|Phe|
| | | | |325| | | |330| | | | |335| | |
|Tyr|Lys|Met|Ile|Lys|Glu|Gly|Phe|Arg|Met|Leu|Ser|Pro|Glu|His|Ala|
| | | |340| | | |345| | | | |350| | | |
|Pro|Ala|Glu|Met|Tyr|Asp|Ile|Met|Lys|Thr|Cys|Trp|Asp|Ala|Asp|Pro|
| | |355| | | |360| | | | |365| | | | |
|Leu|Lys|Arg|Pro|Thr|Phe|Lys|Gln|Ile|Val|Gln|Leu|Ile|Glu|Lys|Gln|
| |370| | | |375| | | | |380| | | | | |
|Ile|Ser|Glu|Ser|Thr|Asn|His|Ile|Tyr|Ser|Asn|Leu|Ala|Asn|Cys|Ser|
|385| | | |390| | | | |395| | | | | |400|
|Pro|Asn|Arg|Gln|Lys|Pro|Val|Val|Asp|His|Ser|Val|Arg|Ile|Asn|Ser|
| | | |405| | | | |410| | | | |415| | |
|Val|Gly|Ser|Thr|Ala|Ser|Ser|Ser|Gln|Pro|Leu|Leu|Val|His|Asp|Asp|
| | | |420| | | |425| | | | |430| | | |
|Val| | | | | | | | | | | | | | | |

(2) INFORMATION FOR SEQ ID NO:10:

(i) SEQUENCE CHARACTERISTICS:
(A) LENGTH: 437 amino acids
(B) TYPE: amino acid
(D) TOPOLOGY: linear (ii) MOLECULE TYPE: peptide (x) PUBLICATION INFORMATION:
(A) AUTHORS: Coussens, L., et al.
(C) JOURNAL: Nature
(D) VOLUME: 320
(F) PAGES: 277-280
(G) DATE: 1986

(xi) SEQUENCE DESCRIPTION: SEQ ID NO:10:

| | | | | | | | | | | | | | | | |
|---|---|---|---|---|---|---|---|---|---|---|---|---|---|---|---|
|Leu|Leu|Tyr|Lys|Tyr|Lys|Gln|Lys|Pro|Lys|Tyr|Gln|Val|Arg|Trp|Lys|
|1| | | |5| | | | |10| | | | |15| |
|Ile|Ile|Glu|Ser|Tyr|Glu|Gly|Asn|Ser|Tyr|Thr|Phe|Ile|Asp|Pro|Thr|
| | | |20| | | | |25| | | | |30| | |
|Gln|Leu|Pro|Tyr|Asn|Glu|Lys|Trp|Glu|Phe|Pro|Arg|Asn|Asn|Leu|Gln|
| | |35| | | | |40| | | | |45| | | |
|Phe|Gly|Lys|Thr|Leu|Gly|Ala|Gly|Ala|Phe|Gly|Lys|Val|Val|Glu|Ala|
| |50| | | | |55| | | | |60| | | | |
|Thr|Ala|Phe|Gly|Leu|Gly|Lys|Glu|Asp|Ala|Val|Leu|Lys|Val|Ala|Val|
|65| | | | |70| | | | |75| | | | |80|
|Lys|Met|Leu|Lys|Ser|Thr|Ala|His|Ala|Asp|Glu|Lys|Glu|Ala|Leu|Met|
| | | | |85| | | | |90| | | | |95| |
|Ser|Glu|Leu|Lys|Ile|Met|Ser|His|Leu|Gly|Gln|His|Glu|Asn|Ile|Val|
| | | |100| | | | |105| | | | |110| | |
|Asn|Leu|Leu|Gly|Ala|Cys|Thr|His|Gly|Gly|Pro|Val|Leu|Val|Ile|Thr|
| | | |115| | | | |120| | | | |125| | |
|Glu|Tyr|Cys|Cys|Tyr|Gly|Asp|Leu|Leu|Asn|Phe|Leu|Arg|Arg|Lys|Ala|
| | |130| | | | |135| | | | |140| | | |
|Glu|Ala|Met|Leu|Gly|Pro|Ser|Leu|Ser|Pro|Gly|Gln|Asp|Pro|Glu|Gly|
|145| | | | |150| | | | |155| | | | |160|
|Gly|Val|Asp|Tyr|Lys|Asn|Ile|His|Leu|Glu|Lys|Lys|Tyr|Val|Arg|Arg|

|   |   |   |   |   | 165 |   |   |   | 170 |   |   |   | 175 |   |   |
|---|---|---|---|---|---|---|---|---|---|---|---|---|---|---|---|
| Asp | Ser | Gly | Phe 180 | Ser | Ser | Gln | Gly | Val 185 | Asp | Thr | Tyr | Val 190 | Glu | Met | Arg |
| Pro | Val | Ser 195 | Thr | Ser | Ser | Asn | Ser 200 | Ser | Phe | Ser | Gln 205 | Asp | Leu | Asp |
| Lys | Glu 210 | Asp | Gly | Arg | Pro 215 | Leu | Glu | Leu | Arg | Asp 220 | Leu | Leu | His | Phe | Ser |
| Ser 225 | Gln | Val | Ala | Gln 230 | Gly | Met | Ala | Phe | Leu 235 | Ala | Ser | Lys | Asn | Cys | Ile 240 |
| His | Arg | Asp | Val | Ala 245 | Ala | Arg | Asn | Val | Leu 250 | Leu | Thr | Asn | Gly | His 255 | Val |
| Ala | Lys | Ile | Gly 260 | Asp | Phe | Gly | Leu | Ala 265 | Arg | Asp | Ile | Met 270 | Asn | Asp | Ser |
| Asn | Tyr | Ile 275 | Val | Lys | Gly | Asn | Ala 280 | Arg | Leu | Pro | Val | Lys 285 | Trp | Met | Ala |
| Pro | Glu 290 | Ser | Ile | Phe | Asp | Cys 295 | Val | Tyr | Thr | Val | Gln 300 | Ser | Asp | Val | Trp |
| Ser 305 | Tyr | Gly | Ile | Leu | Leu 310 | Trp | Glu | Ile | Phe | Ser 315 | Leu | Gly | Leu | Asn | Pro 320 |
| Tyr | Pro | Gly | Ile | Leu 325 | Val | Asn | Ser | Lys | Phe 330 | Tyr | Lys | Leu | Val | Lys 335 | Asp |
| Gly | Tyr | Gln | Met 340 | Ala | Gln | Pro | Ala | Phe 345 | Ala | Pro | Lys | Asn | Ile 350 | Tyr | Ser |
| Ile | Met | Gln 355 | Ala | Cys | Trp | Ala | Leu 360 | Glu | Pro | Thr | His | Arg 365 | Pro | Thr | Phe |
| Gln | Gln 370 | Ile | Cys | Ser | Phe | Leu 375 | Gln | Glu | Gln | Ala | Gln 380 | Glu | Asp | Arg | Arg |
| Glu 385 | Arg | Asp | Tyr | Thr | Asn 390 | Leu | Pro | Ser | Ser | Ser 395 | Arg | Ser | Gly | Gly | Ser 400 |
| Gly | Ser | Ser | Ser | Ser 405 | Glu | Leu | Glu | Glu | Glu 410 | Ser | Ser | Ser | Glu | His 415 | Leu |
| Thr | Cys | Cys | Glu 420 | Gln | Gly | Asp | Ile | Ala 425 | Gln | Pro | Leu | Leu | Gln 430 | Pro | Asn |
| Asn | Tyr | Gln 435 | Phe | Cys |   |   |   |   |   |   |   |   |   |   |   |

(2) INFORMATION FOR SEQ ID NO:11:

(i) SEQUENCE CHARACTERISTICS:
      (A) LENGTH: 566 amino acids
      (B) TYPE: amino acid
      (D) TOPOLOGY: linear (ii) MOLECULE TYPE: peptide (x) PUBLICATION INFORMATION:
      (A) AUTHORS: Gronwald, R., et al.
      (C) JOURNAL: Proc. Natl. Acad. Sci. U.S.A.
      (D) VOLUME: 85
      (F) PAGES: 3435-3439
      (G) DATE: 1988

(xi) SEQUENCE DESCRIPTION: SEQ ID NO:11:

|   |   |   |   |   |   |   |   |   |   |   |   |   |   |   |   |
|---|---|---|---|---|---|---|---|---|---|---|---|---|---|---|---|
| Met 1 | Leu | Trp | Gln | Lys 5 | Lys | Pro | Arg | Tyr | Glu 10 | Ile | Arg | Trp | Lys | Val 15 | Ile |
| Glu | Ser | Val | Ser 20 | Ser | Asp | Gly | His | Glu 25 | Tyr | Ile | Tyr | Val | Asp 30 | Pro | Val |
| Gln | Leu | Pro 35 | Tyr | Asp | Ser | Thr | Trp 40 | Glu | Leu | Pro | Arg | Asp 45 | Gln | Leu | Val |

```
Leu Gly Arg Thr Leu Gly Ser Gly Ala Phe Gly Gln Val Val Glu Ala
     50                  55                  60
Thr Ala His Gly Leu Ser His Ser Gln Ala Thr Met Lys Val Ala Val
 65                  70                  75                  80
Lys Met Leu Lys Ser Thr Ala Arg Ser Ser Glu Lys Gln Ser Leu Met
                 85                  90                  95
Ser Glu Leu Lys Ile Met Ser His Leu Gly Pro His Leu Asn Val Val
                100                 105                 110
Asn Leu Leu Gly Ala Cys Thr Lys Gly Gly Pro Ile Tyr Ile Ile Thr
             115                 120                 125
Glu Tyr Cys Arg Tyr Gly Asp Leu Val Asp Tyr Leu His Arg Asn Lys
    130                 135                 140
His Thr Phe Leu Gln Arg His Ser Asn Lys His Cys Pro Pro Ser Ala
145                 150                 155                 160
Glu Leu Tyr Ser Asn Ala Leu Pro Val Gly Phe Ser Leu Pro Ser His
                165                 170                 175
Leu Asn Leu Thr Gly Glu Ser Asp Gly Gly Tyr Met Asp Met Ser Lys
            180                 185                 190
Asp Glu Ser Ile Asp Tyr Val Pro Met Leu Asp Met Lys Gly Asp Ile
    195                 200                 205
Lys Tyr Ala Asp Ile Glu Ser Pro Ser Tyr Met Ala Pro Tyr Asp Asn
    210                 215                 220
Tyr Val Pro Ser Ala Pro Glu Arg Thr Tyr Arg Ala Thr Leu Ile Asn
225                 230                 235                 240
Asp Ser Pro Val Leu Ser Tyr Thr Asp Leu Val Gly Phe Ser Tyr Gln
                245                 250                 255
Val Ala Asn Gly Met Asp Phe Leu Ala Ser Lys Asn Cys Val His Arg
            260                 265                 270
Asp Leu Ala Ala Arg Asn Val Leu Ile Cys Glu Gly Lys Leu Val Lys
    275                 280                 285
Ile Cys Asp Phe Gly Phe Ala Arg Asp Ile Met Arg Asp Ser Asn Tyr
290                 295                 300
Ile Ser Lys Gly Ser Thr Tyr Leu Pro Leu Lys Trp Met Ala Pro Glu
305                 310                 315                 320
Ser Ile Phe Asn Ser Leu Tyr Thr Thr Leu Ser Asp Val Trp Ser Phe
                325                 330                 335
Gly Ile Leu Leu Trp Glu Ile Phe Thr Leu Gly Gly Thr Pro Tyr Pro
            340                 345                 350
Glu Leu Pro Met Asn Asp Gln Phe Tyr Asn Ala Ile Lys Arg Gly Tyr
    355                 360                 365
Arg Met Ala Gln Pro Ala His Ala Ser Asp Glu Ile Tyr Glu Ile Met
370                 375                 380
Gln Lys Cys Trp Glu Glu Lys Phe Glu Thr Arg Pro Pro Phe Ser Gln
385                 390                 395                 400
Leu Val Leu Leu Leu Glu Arg Leu Leu Gly Glu Gly Tyr Lys Lys Lys
                405                 410                 415
Tyr Gln Gln Val Asp Glu Glu Phe Leu Arg Ser Asp His Pro Ala Ile
            420                 425                 430
Leu Arg Ser Gln Ala Arg Phe Pro Gly Ile His Ser Leu Arg Ser Pro
    435                 440                 445
Leu Asp Thr Ser Ser Val Leu Tyr Thr Ala Val Gln Pro Asn Glu Ser
450                 455                 460
Asp Asn Asp Tyr Ile Ile Pro Leu Pro Asp Pro Lys Pro Asp Val Ala
```

```
                465                         470                         475                         480

Asp Glu Gly Leu Pro Glu Gly Ser Pro Ser Leu Ala Ser Ser Thr Leu
                          485                     490                 495

Asn Glu Val Asn Thr Ser Ser Thr Ile Ser Cys Asp Ser Pro Leu Glu
                          500                     505                 510

Leu Gln Glu Glu Pro Gln Gln Ala Glu Pro Glu Ala Gln Leu Glu Gln
                      515                 520                 525

Pro Gln Asp Ser Gly Cys Pro Gly Pro Leu Ala Glu Ala Glu Asp Ser
                      530                 535                 540

Phe Leu Glu Gln Pro Gln Asp Ser Gly Cys Pro Gly Pro Leu Ala Glu
          545                     550                     555                 560

Ala Glu Asp Ser Phe Leu
                          565
```

( 2 ) INFORMATION FOR SEQ ID NO:12:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

TCGACGCGCG ATGGAG        16

SCREENING METHOD USING A RECOMBINANT KINASE INSERT DOMAIN CONTAINING RECEPTOR AND GENE ENCODING SAME

This is a divisional of copending application Ser. No. 07/930,548 filed on Nov. 23, 1992.

FIELD OF THE INVENTION

This invention relates to the DNA sequence encoding a novel human growth factor receptor which is a type III receptor tyrosine kinase. The receptor is referred to as Kinase insert Domain containing Receptor (KDR) and binds specifically to the growth factor vascular endothelial cell growth factor (VEGF). This invention also relates to the amino acid sequence of the receptor.

BACKGROUND OF THE INVENTION

Growth factors are small molecules which regulate normal cell growth and development through interaction with cell surface receptors. The receptors for a number of growth factors are referred to as tyrosine kinases; that is, binding of growth factor to the receptor stimulates an increased phosphorylation of tyrosine amino acids within the receptor; this is turn leads to cellular activation (Bibliography 1).

There is increasing evidence that genetic alterations affecting the expression of receptor tyrosine kinases (RTK) can contribute to the altered cell growth associated with cancer. This conclusion is supported by the frequent identification of RTK as products of the oncogenes for many of the acutely transforming retroviruses (e.g., 2,3,4) and the overexpression of RTK in certain cancers (5). The identification of a novel RTK may lead to a better understanding of cell growth under both normal and transforming circumstances.

The amino acid sequence in the catalytic domain of all tyrosine kinases has been conserved (6). Detailed analysis of the amino acid sequences within the catalytic and noncatalytic domains of RTK indicates the existence of distinct structural subtypes. One group of RTK (designated type III) includes the ckit proto-oncogene and the receptors for platelet derived growth factor (PDGF) and colony stimulating factor-1 (CSF-1).

The most unusual feature of this subtype is that its catalytic (kinase) domain is interrupted by a long insertion sequence of 12–102 amino acids (the kinase insert domain) The two peptides constituting the kinase domain are conserved between the receptors, while the sequence of the kinase insert domain is unique for each receptor.

Several approaches have been tried in order to identify novel RTK, including low-stringency screening of cDNA libraries with previously characterized DNA probes (7). More recently, a technique has been developed that is capable of greatly facilitating the identification of novel genes for which some sequence data are known. The polymerase chain reaction (PCR) has been used to identify novel members of several gene families including those of guanine nucleotide regulatory proteins (8) and protein phosphatases (9). PCR has been used to identify novel tyrosine kinase genes (10), though the primers used in that study were designed from DNA segments contained in all tyrosine kinases, rather than being specifically directed against RTK. It is a continuing goal to identify receptors for growth factors.

The elucidation of the growth factors, as well as their receptors, involved in regulating endothelial cell function is critical for the understanding of how new blood vessels are formed (angiogenesis). Angiogenesis plays a significant role in both normal and pathological events such as embryogenesis, progression of ocular diseases, and wound healing (11). In particular, angiogenesis is an important process for the growth of tumors (11). Angiogenesis is a complex process involving endothelial cell proliferation, migration, and tissue infiltration. These events are stimulated by growth factors which either (i) act directly on endothelial cells (12,13), or (ii) act indirectly by inducing host cells to release specific endothelial cell growth factors (11). One member of the first group is vascular endothelial cell growth factor (VEGF), also known as vascular permeability factor (14–16). Besides its angiogenic activity, VEGF displays the physiological function of increasing the permeability of capillary vessels to different macromolecules (14).

SUMMARY OF THE INVENTION

The present invention relates to novel DNA segments which together comprise a gene which encodes type III RTK. The type III RTK encoded by the gene is designated the KDR protein (which stands for Kinase insert Domain containing Receptor). The KDR protein binds specifically to the growth factor VEGF (vascular endothelial cell growth factor).

The DNA segments are identified and isolated through the use of PCR technology. The overall strategy is summarized as follows:

PCR is used to amplify the DNA segments corresponding to the kinase insert domains of type III receptor tyrosine kinase genes in an endothelial cell library designated HL10246 (Clontech Laboratories, Inc., Palo Alto, Calif.). Degenerate oligonucleotide primers are designed which are complementary to conserved tyrosine kinase domains flanking the kinase insert domains of known type III receptor tyrosine kinases. These primers are used in the PCR procedure. DNA probes, designed from the DNA sequence of the PCR product, are then used to identify cDNA clones of the receptor gene from the original cDNA library.

In particular, the present invention relates to specific oligonucleotides which, when used as primers for PCR, allow for the amplification of DNA segments corresponding to the kinase insert domains of type III RTK genes.

In a principal embodiment, the present invention is directed to three overlapping DNA segments (designated BTIII081.8, BTIII129.5 and BTIV169) which comprise the entire coding region of this novel gene, namely, 4,068 nucleotides extending to the 3' end.

These DNA segments are isolated from a human endothelial cell cDNA library and together comprise the gene coding for a novel type III receptor tyrosine kinase. The human gene containing these DNA segments is referred to hereinafter as KDR (which stands for Kinase insert Domain containing Receptor) or, alternatively, as kdp (which stands for Kinase insert Domain containing Protein). The se of the term KDR is intended to include any DNA segments which form the human gene which encodes the novel type III RTK of this application.

The DNA segments embodied in this invention are isolated from human sources. The present invention comprises DNA segments, and methods for using these DNA segments, which allow for the identification of a closely related gene in mouse DNA. The methods developed in this invention can be readily used by those skilled in the art for the identification and isolation of closely-related homologues in other species. Therefore, the present invention also embodies all DNA segments from species other than human which encode proteins having substantially the same amino acid sequence as that encoded by the kdp gene.

The present invention further relates to methods developed for the detection of mRNA's produced as a result of transcription of the sense strands of the DNA segments of this invention. Messenger RNA prepared from bovine endothelial cells are used in developing these methods. The ability to detect mRNA for a novel RTK may ultimately have medical benefit, especially in light of recent observations that the mRNA for certain RTKs are overexpressed in some cancers (5).

The methods developed in the present invention for detecting mRNA expressed by the kdp gene can be readily used by those of ordinary skill in the art for the detection of mRNA species related to the kdp gene in any cell type and from any species. For this reason, the present invention embodies all mRNA segments which are the result of transcription of the kdp gene.

The present invention relates to methods for expression of the receptor protein, for example, in CMT-3 cells of monkey kidney origin. The receptor protein, portions thereof, and mutated forms of the receptor protein may be expressed in many other cells by those skilled in the art using methods similar to those described in this application. For this reason, the present invention embodies all proteins encoded by the human KDR gene and proteins encoded by related genes found in other species.

The present invention further relates to methods for studying the interaction of VEGF to the expressed KDR protein. Recent work in the literature (17) indicates that VEGF is one member of a family of related proteins, and the interaction of growth factors similar to VEGF with the KDR protein can readily be studied by those skilled in the art using methods similar to those described in this application. These methods can readily be modified to study the interaction of candidate pharmaceuticals with the KDR protein towards the goal of developing an antagonist or agonist of VEGF action. For this reason, the present invention embodies methods for studying the interaction of VEGF and VEGF-related growth factors with the KDR protein.

BRIEF DESCRIPTION OF THE DRAWINGS

FIG. 2 depicts the two sets of primers used for PCR (SEQ ID NO: 1 and 2). The nucleotide sequences in appropriate regions of the four known type III receptor tyrosine kinase cDNAs are aligned and degenerate oligonucleotide primers are designed based upon the consensus sequences.

FIGS. 4A and 4B depict the DNA sequence of the two PCR products (Panel A: 363 bp segment derived from the 420 bp product (SEQ ID NO: 3); Panel B: 251 bp product (SEQ ID NO: 4)). The two products are purified by agarose gel electrophoresis, digested with SalI and EcoRI, and cloned into the plasmid vector pBlueScribe(+)™ (Strategene; San Diego, Calif.). The 420 bp PCR product is digested to 363 bp during this procedure. The DNA sequences for the primers used in the amplification are underlined.

FIG. 5A depicts a computer assisted comparison of the DNA sequence for the 363 bp DNA segment derived from the 420 bp PCR product with the sequence of a DNA segment of the PDGF receptor (SEQ ID NO: 5) (18). A region of strong homology between the 363 bp segment derived from the 420 bp PCR product and the PDGF receptor is contained in a box. FIG. 5B depicts a computer assisted comparison of the DNA sequence for the 251 bp PCR product with the sequence of a DNA segment of the FGF receptor (SEQ ID NO: 6) (7).

FIGS. 7A through 7M depict the DNA and predicted amino acid sequence of KDR, plus the stop codon (nucleotides 1–4071 of SEQ ID NO: 7). The sequence of the DNA segment amplified by PCR is underlined (nucleotides 2749–3105 of SEQ ID NO: 7). Cysteine residues in the putative extracellular domain are circled. Potential N-linked glycosylation sites are indicated by an asterisk. The putative membrane spanning region is enclosed in a box (nucleotides 2293–2367 of SEQ ID NO: 7).

FIGS. 9A and 9B depict a comparison of the predicted amino acid sequence in the putative intracellular portion of the KDR protein to the ckit proto-oncogene (SEQ ID No: 8) (3), the CSF-1 receptor (SEQ ID NO: 9) (4), and the PDGF receptor (SEQ ID NO: 10) (18). Exact matches are indicated by an asterisk. Gaps are introduced to achieve maximum alignment. The putative ATP recognition site is indicated by three asterisks.

DETAILED DESCRIPTION OF THE INVENTION

Figure 1:
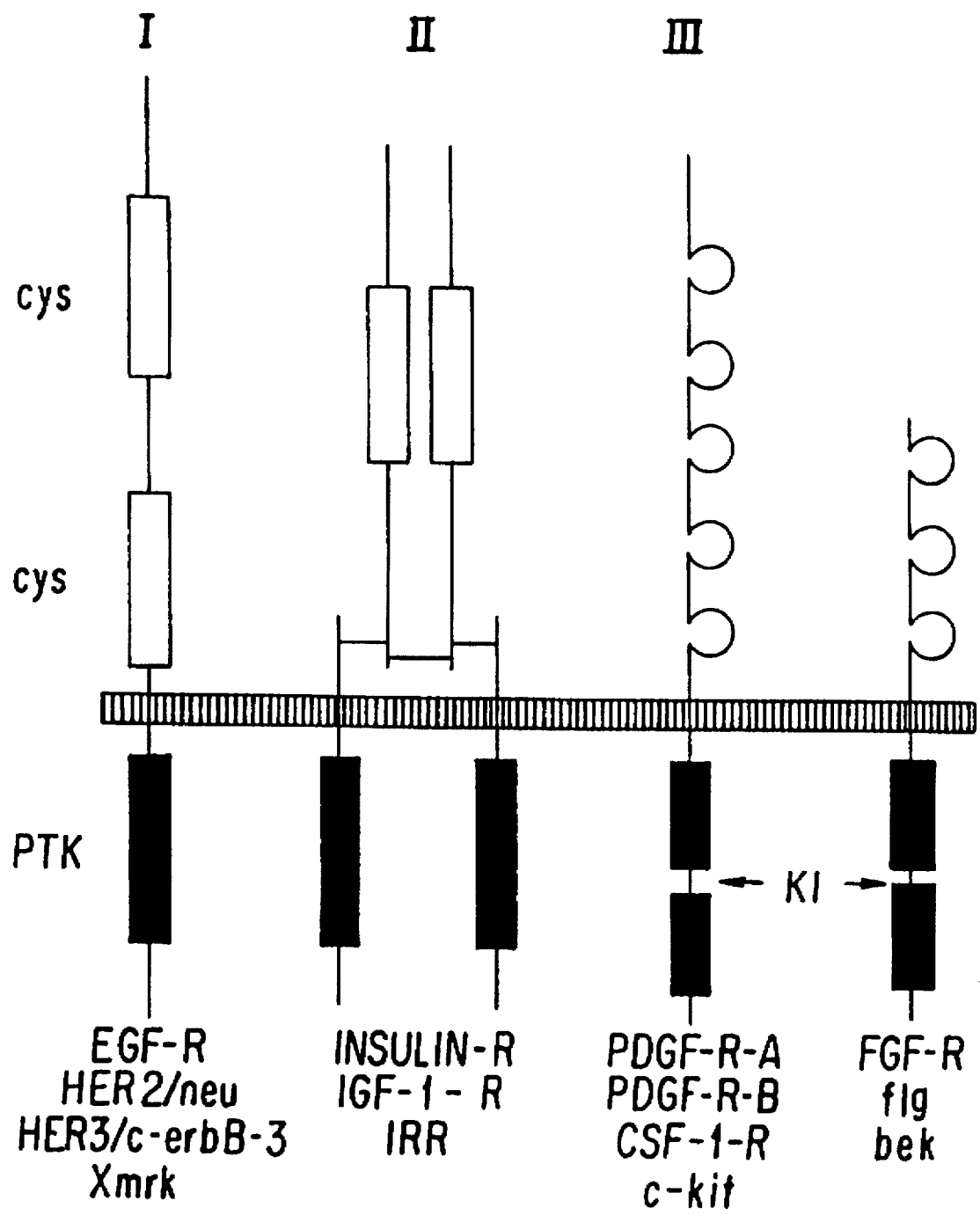
FIG. 1 depicts a schematic representation of three receptor tyrosine kinase subclasses (6). KI is kinase insert domain; PTK is kinase domain; cys is cysteine rich region.

The strategy used to discover the DNA segments for the novel type III RTK gene begins with the design of two degenerate oligonucleotide primers based upon their homology to specific regions of the kinase domains of known RTK genes (FIG. 2) (3,4,7,18). In one embodiment, the polymerase chain reaction is then used to amplify DNA segments from a human endothelial cell cDNA library (designated HL 10246). The cDNA products from this step are each cloned into a plasmid vector designated pBlueScribe(+)™ (Strategene, San Diego, Calif.) and sequenced. Oligonucleotide probes are designed from potentially interesting sequences in order to screen the cDNA library for more full length clones of the novel cDNA.

The strategy just described provides several novel elements: 1) the DNA sequences of the oligonucleotide primers used during PCR; 2) the DNA sequence of the products generated by the polymerase chain reaction; and 3) the DNA sequence of the final cloned DNA segments. Each of these elements of the invention described in this application will now be discussed in detail.

FIG. 2 shows the rationale for choosing the oligonucleotide primers used in the PCR. The primers are designed to allow for the PCR amplification of the kinase insert domain of type III RTK genes. In order to design the primers, the DNA sequences of known type III RTK genes are aligned in specific regions of their catalytic domains, and a consensus sequence is chosen. The regions of the catalytic domains chosen in designing the primers flank the kinase insert domains of the receptor genes.

Primer 1 (SEQ ID No: 1) is designed from a region of the kinase domain 5' to the kinase insert domain, and consists of a mixture of four different 21mers. Primer 2 (SEQ ID NO: 2) is designed from a region of the kinase domain 3' to the kinase insert domain, and consists of a mixture of sixteen different 29mers with one inosine, indicated in SEQ ID NO: 2 by "N".

SalI and EcoRI restriction sites are included at the 5' end of primers 1 and 2, respectively, to facilitate the subcloning of the amplified PCR products into plasmid vectors. Those skilled in the art may use other restriction sites; other minor modifications in the protocol above permits the design of primers without the inclusion of restriction sites.

The selection of these specific primers constitutes a novel approach towards identifying novel type III RTK genes. It had previously been shown (10) that primers designed from DNA sequences common to all tyrosine kinases allows for the identification of novel proteins. The present invention is the first to contemplate the use of PCR to specifically target type III RTK.

The protocol used for PCR is as follows: Human endothelial cell cDNA (designated HL10246) is denatured by boiling and submitted to 30 cycles of PCR using 1 nmol of both primers in a final volume of 100 ml. The timing is 1.5 minutes at 92° C., 2 minutes at 50° C., and 2 minutes at 74° C. DNA from 5 ml of sample is separated on a 1% agarose gel and stained with ethidium bromide.

Figure 3:
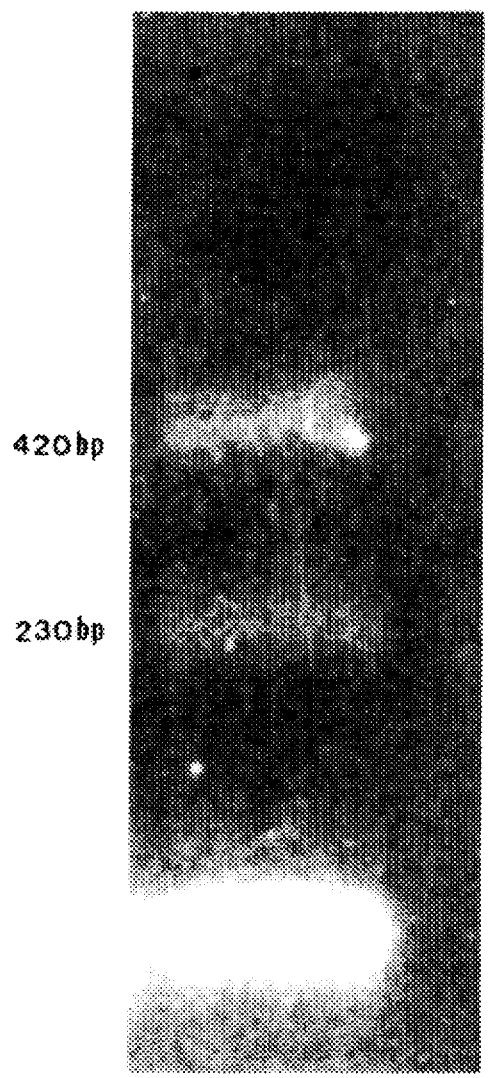
FIG. 3 depicts the amplification of the kinase insert domains using PCR. DNA segments encoding the kinase insert domains of type III receptor tyrosine kinases are amplified by PCR. A sample (5 ml) is run on a 1.0% agarose gel which is stained with ethidium bromide. DNA size standards (123 bp ladder; Bethesda Research Laboratories, Bethesda, Md.) are run as well.

FIG. 3 shows the results of the PCR amplification. Two DNA products, with sizes 251 bp (SEQ ID NO: 4) and 420 bp, are visible when a sample of the reaction is electrophoresed on a 1.0% agarose gel and stained with ethidium bromide. The sizes of the two products are within the range expected for type III RTK genes (products derived from the FGF and PDGF receptor genes, which have the smallest and largest known kinase insert domains, would be 230 and 510 bp, respectively (20, 21).

Figures 4A, 4B:
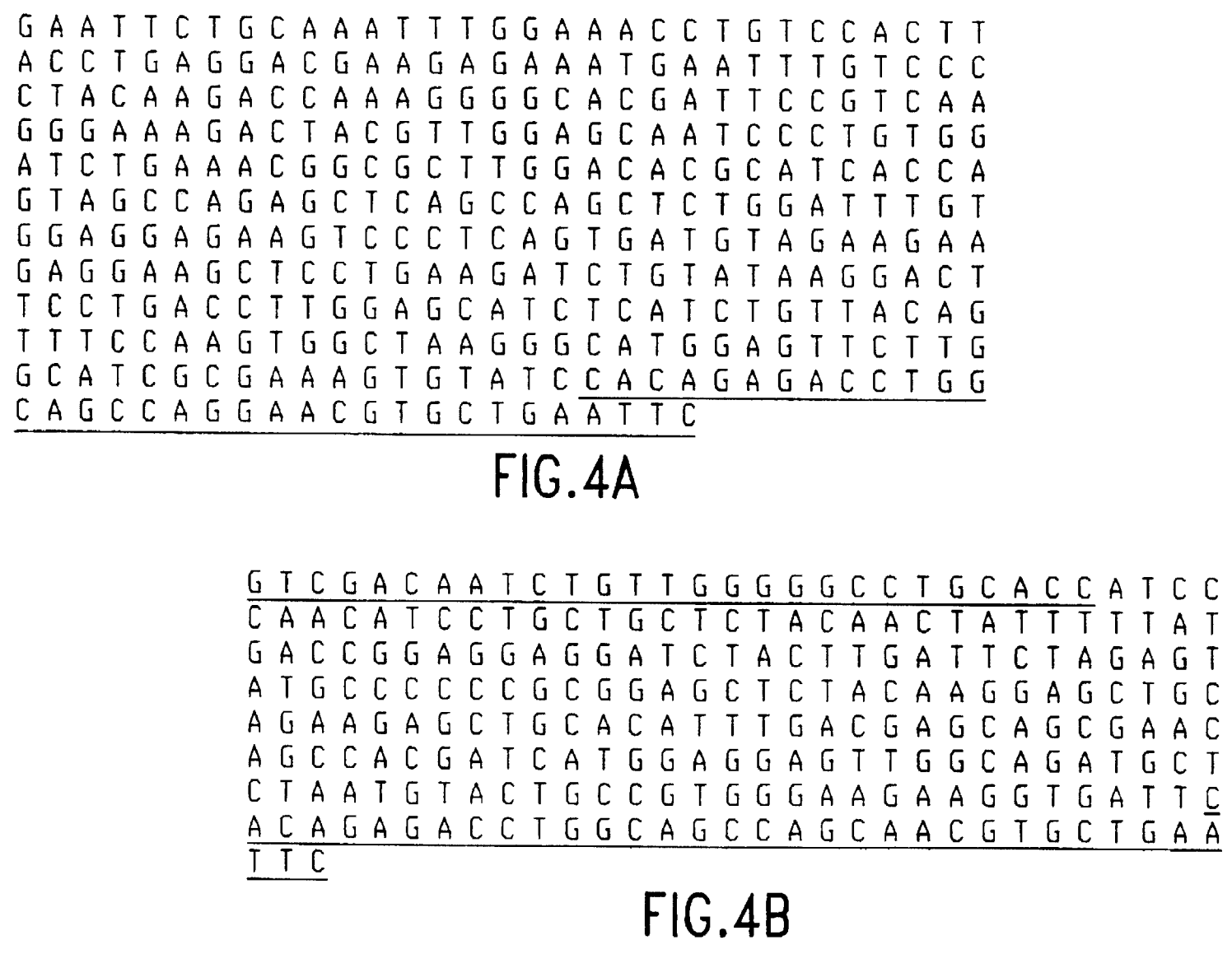

The DNA from four contiguous lanes with sizes ranging from 200 to 600 bp is electrophoresed onto DEAE filter paper, eluted from the paper with salt, and ethanol precipitated. The samples are incubated with 5 units of EcoRI and SalI. The restriction enzymes digest the 420 bp DNA segment to a 363 bp DNA segment (SEQ ID NO: 3), due to the presence of an EcoRI site within the 420 bp DNA segment (nucleotide 2749, SEQ ID NO: 7). The restriction enzyme digested PCR products are then subcloned into the plasmid vector pBlueScribe(+)™. The recombinant clones are analyzed by sequencing using the dideoxy-method (22) using a United States Biochemical (Cleveland, Ohio) Sequenase Version 2.0 sequencing kit. FIG. 4 shows the DNA sequences for the 251 bp PCR product and the 363 bp DNA segment derived from the 420 bp PCR product.

Figure 5A:
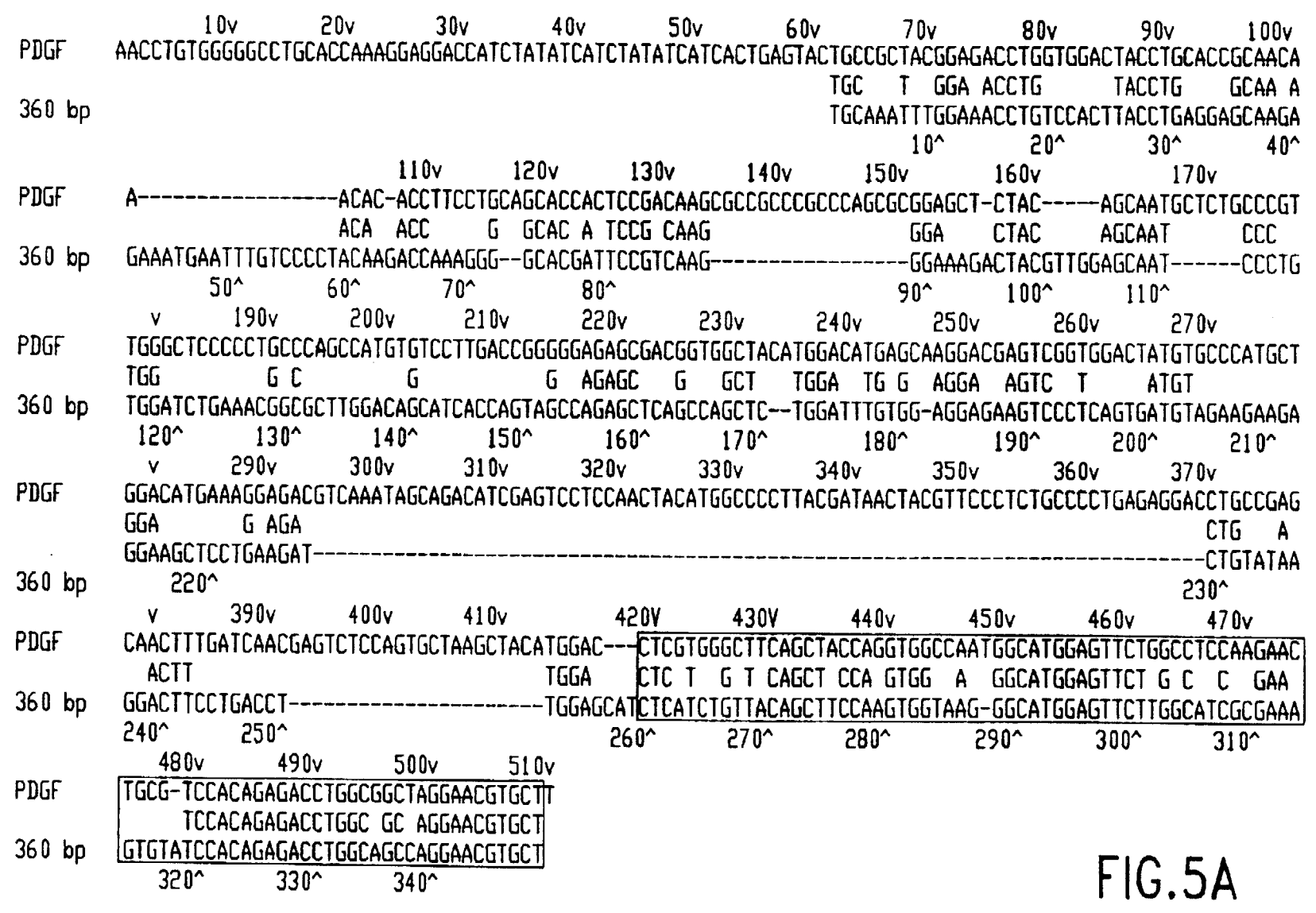

Computer assisted comparison of the DNA sequence for the 363 bp segment of the 420 bp PCR product to databases of known DNA sequences reveals that the sequence is novel, because it shares strong sequence identity with the flanking catalytic domain of known type III RTK genes, but not their kinase insert domains. FIG. 5A compares the DNA sequence for the 363 DNA segment with that for the PDGF receptor gene (SEQ ID No: 5). Similar results are obtained using other type III RTK genes.

Figure 5B:
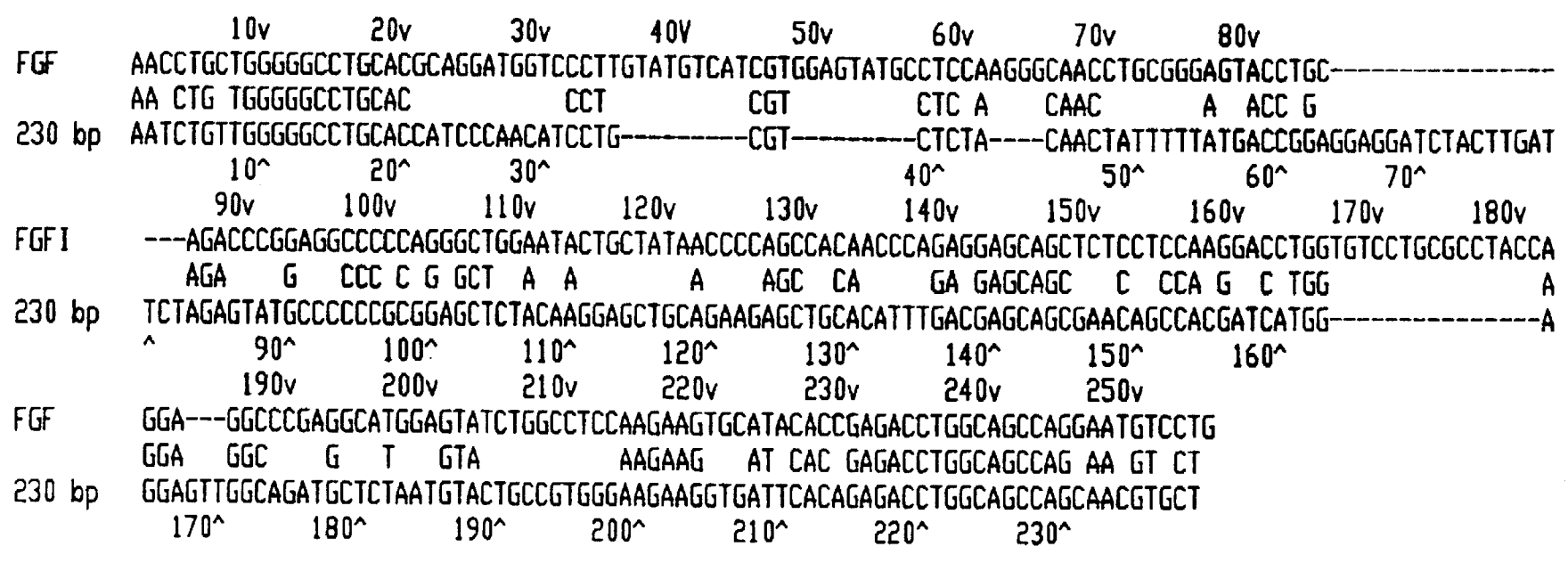

DNA sequencing of the 251 bp PCR product reveals a novel sequence containing both primers used for the amplification, but the sequence shows little homology to known tyrosine kinases. This is depicted in FIG. 5B, which compares the DNA sequence for the 251 bp DNA segment with that for the FGF receptor (SEQ ID NO: 6). For this reason, further analysis of Product 1 is not pursued.

The protocols used during the PCR do not allow for amplification of the kinase insert domains of known receptor tyrosine kinases in the endothelial cell library used because of the low copy number of the message present in the library. There have been many studies on the effect of FGF on endothelial cell function (23,24) although there is evidence that the expression of the FGF receptor is developmentally regulated (7) and it is likely that the library used contains little or no cDNA for the FGF receptor.

An oligonucleotide probe, designed from the DNA sequence of the 363 bp segment, is synthesized (using an ABI 380 DNA Synthesizer) in order to screen the human endothelial cell cDNA library (HL10246) for the isolation of more full length clones containing the 363 bp DNA segment. The probe sequence is chosen from the region of the 363 bp DNA segment which shares little sequence homology with known RTK.

The screening of the endothelial cell cDNA library is conducted as follows: Lambda gt11 phage, $10^6$, are adsorbed to *E. coli* LE392 for 15 minutes at 37° C. prior to plating onto agar plates at a density of $5\times10^5$ phage per plate. After allowing the phage plaques to develop at 37° C., plaque lifts are made using nitrocellulose filters, denatured in 0.4N NaCl for 1 minute, and neutralized in 0.5M Tris.HCl, pH 7.3, plus 1.5M NaCl. The filters are washed with 2×standard saline citrate (SSC) and then baked for 1.5 hour in a vacuum oven at 80° C. The filters are probed with an [$^{32}$P] ATP end labeled synthetic oligonucleotide, 5'-TTTCCCTTGACGGAATCGTGCCTTTGGT-3', which is the reverse complement of a DNA sequence contained in the PCR amplified product (FIG. 3). Hybridization is performed at 50° C. in 5×SSPE (167 mM NaCl, 10 mM sodium phosphate, pH 7.4, 1 mM EDTA), 2.5×Denhardts, 0.5% sodium dodecyl sulfate (SDS), 100 mg/ml salmon sperm DNA. The filters are washed twice, 20 minutes per wash, with 2×SSC plus 0.1% SDS at room temperature, followed by washing twice at 50° C. with 0.1×SSC plus 0.1% SDS; 20 minutes per wash. Positive clones are identified, picked and plaque purified.

Forty-five positive clones are obtained. Three of these positive clones are plaque purified and their phage DNA isolated. Digestion of the DNA with EcoRI and electrophoresis in agarose indicates that one clone, designated BTIII081.8, contains the largest insert, and subsequent analysis indicates that the DNA insert of this clone overlaps that of the inserts contained in other two purified clones (designated BTIII079.11 and BTIII079.47A).

Figure 6:
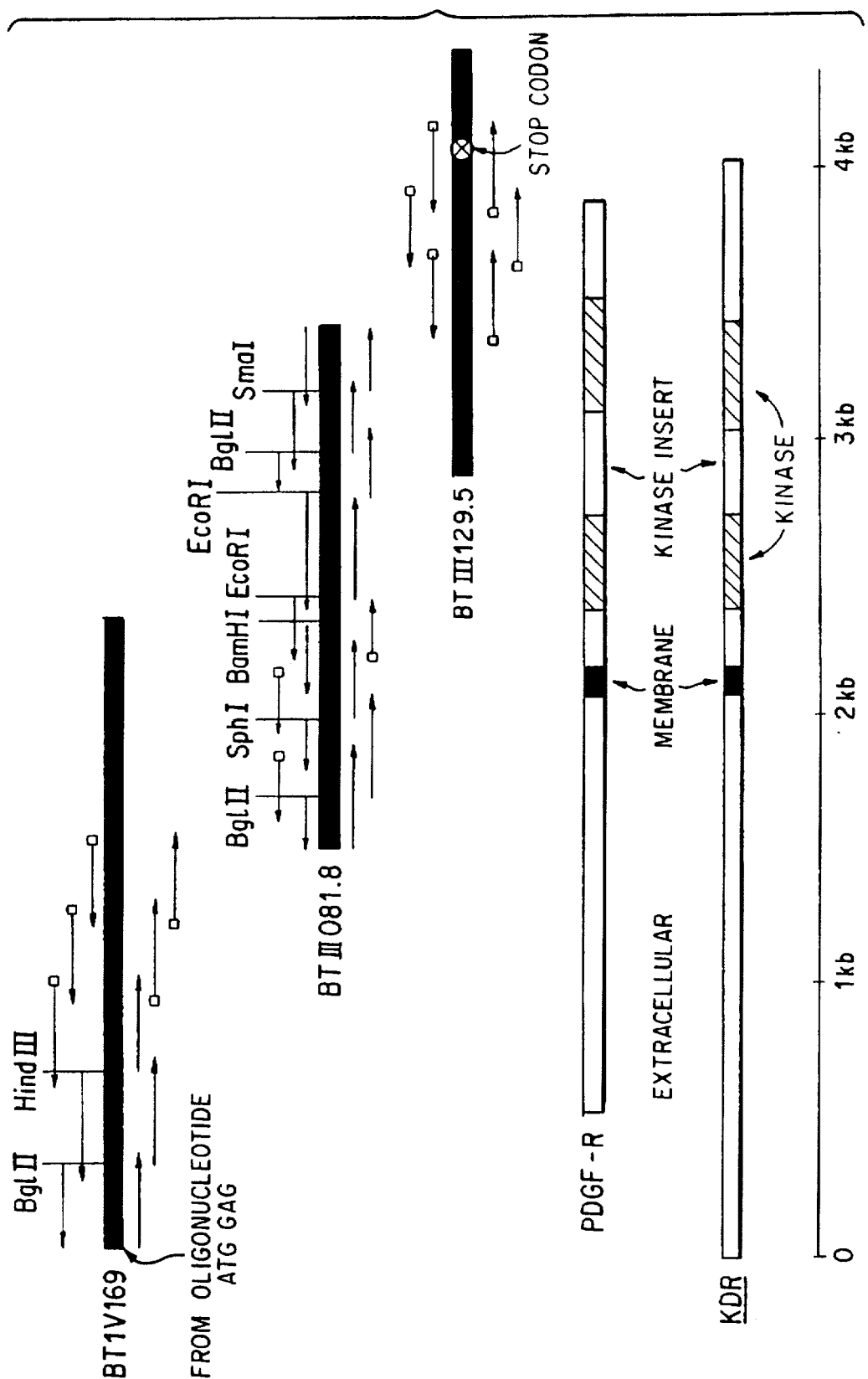
FIG. 6 depicts the strategy used for sequencing the insert portions of clones BTIII081.8 and BTIII129.5 and BTIV169. The sequencing reaction uses either synthetic oligonucleotides (represented by boxes at the start of an arrow), or the M13 universal primer (no box) to initiate the reaction. In some cases, portions of these DNA segments are isolated using the restriction enzymes indicated in the figure, and subcloned back into the plasmid vector pUC118, so that the M13 universal primer can be used. The position of the stop codon in BTIII129.5 is indicated. The coding portions of these DNA segments are shown at the bottom of the figure. The relative positions of the 1) membrane spanning portion, 2) kinase domains, and 3) kinase insert domain are indicated. The position of these structural features within the KDR derived DNA segments is compared in relation to their position in the PDGF-receptor ("PDGF-R").

Digestion of the purified phage DNA of the clone designated BTIII081.8 with EcoRI results in DNA segments of 250 bp, 600 bp, and 1000 bp. Each of these three products is subcloned into the plasmid vector pUC118 and sequenced (FIG. 6 shows the strategy used for sequencing). The orientation of the three fragments is determined by subcloning from the insert a BglII/BglII fragment into pUC118 and sequencing across the EcoRI junctions using a synthetic oligonucleotide to prime the sequencing reaction.

A restriction map is determined for each fragment (FIG. 6). Various restriction site pieces are removed from the plasmids and recloned into pUC118 so that sequencing the resulting plasmids with the universal primer allows for sequencing most of the entire original fragments in both directions. Three oligonucleotide primers are required to sequence the entire cDNA in both directions. For the purposes of this application, this insert contains nucleotides numbered 1510–3406 (SEQ ID NO. 7).

A [$^{32}$P|CTP-labelled, nick-translated EcoRI-BamHI DNA segment derived from clone BTIII081.8 (nucleotides 1510–2417 of SEQ ID NO. 7) is used as a probe to rescreen the original endothelial cell cDNA library for more 5' full length DNA segments of the gene from which the insert portion of BTIII081.8 is derived. The protocols used to isolate the overlapping clones are identical to that used to isolate BTIII081.8.

A synthetic oligonucleotide probe is designed with 29 nucleotides corresponding to part of the DNA sequence of the insert portion of the clone BTIII081.8 (nucleotides 3297–3325 of SEQ ID NO. 7) in order to rescreen the original endothelial cell cDNA library for more full 3' length DNA segments of the gene from which the insert portion of BTIII081.8 is derived. The protocols used to isolate the overlapping clones are identical to that used to isolate BTIII081.8. Several positive clones for each of the 5' and 3' ends are identified and plaque purified.

One of the clones is designated BTIII200.2. The DNA from BTIII200.2 contains a 3.4 kb insert as determined by EcoRI digestion of the isolated phage DNA. EcoRI digestion of BTIII200.2 results in three DNA fragments. One of these fragments (2.5 kb) is cloned into pUC119 and is designated BTIV006. The clone BTIV006 contains nucleotides numbered 7–2482. As described below, BTIV006 plus nucleotides 1–6 is designated BTIV169. DNA sequencing of the 2.5 kb DNA insert (BTIV169) indicates that it overlaps over one thousand nucleotides of the DNA sequence of the insert portion of the clone BTIII081.8 (FIG. 6) at the 5' end.

A second clone isolated from the cDNA library is designated BTIII129.5. The DNA from BTIII129.5 contains a 2.2 kb insert as determined by EcoRI digestion of the isolated phage DNA. DNA sequencing of the 2.2 kb DNA insert indicates that it overlaps over five hundred nucleotides of the DNA sequence of the insert portion of the clone BTIII081.8 (FIG. 6). The clone BTIII129.5 contains nucleotides numbered 2848–4236 (SEQ ID NO. 7). The DNA sequence for BTIII129.5 contains the stop codon TAA, defining the position of the 3' end of an open reading frame for the novel gene. Except for the first six nucleotides of the gene which are discussed below, these three clones define a gene encoding a growth factor receptor. These three clones define a 4,062 nucleotide sequence of the open reading frame of the gene extending to the 3' end, followed by a 168 nucleotide non-coding region (SEQ ID NO. 7). A sample of a lambda gt11 phage harboring the clone BTIII081.8 has been deposited with the American Type Culture Collection, 12301 Parklawn Drive, Rockville, Md. 20852, U.S.A., and has been assigned ATCC accession number 40,931. A sample of a lambda gt11 phage harboring the clone BTIII129.5 has been deposited with the American Type Culture Collection and has been assigned ATCC accession number 40,975. For reasons discussed below, a sample of the clone BTIV006 was not deposited.

The aforementioned DNA segments (BTIII081.8, BTIII129.5, and BTIII200.2 (or BTIV006) encode 4062 nucleotides of the coding portion of a novel gene. The cDNA clones are incomplete in that a transcription initiation coding for methionine is missing. After the isolation of these clones, Matthews et al. (25) reported the cloning of a gene homologue of KDR in mouse, which was referred to as Flk-1. Analysis of the nucleic acid and amino acid sequence of Flk-1 indicated that the addition of six nucleotides to the 5' end of the isolated KDR clones would provide for a complete coding region.

To achieve this, an EcoRI-BamHI restriction fragment of BTIV200.2 is cloned into the plasmid pBlueScript KS™ (Strategene, La Jolla, Calif.). The 5' end of the inserted DNA is blunt ended with Klenow polymerase and Mung Bean nuclease. Next, the synthetic oligonucleotide TCGACGCGCG ATG GAG (SEQ ID NO. 11) is cloned into this vector. The oligonucleotide contains the sequence ATG GAG in frame with the downstream DNA insert. These nucleotides (ATG GAG) encode the amino acids methionine and glutamic acid, the first two amino acids encoded by the KDR gene. The resulting plasmid vector is designated BTIV140. This plasmid is purified on a CsCl gradient.

The purified plasmid is designated BTTV169. The insert of BTTV169 contains nucleotides 1-2400 (SEQ ID NO. 7) of the KDR gene. A sample of the plasmid pBlueScript KS™ which contains the clone BTTV169 has been deposited with the American Type Culture Collection and has been assigned ATCC accession number 75200.

Thus, together the clones BTIII081.8, BTIII129.5 and BTTV169 comprise the entire open reading frame of 4,068 nucleotides for the novel KDR gene. As will be discussed below, the KDR gene expresses the novel KDR receptor which binds specifically to the growth factor VEGF.

Figure 8:
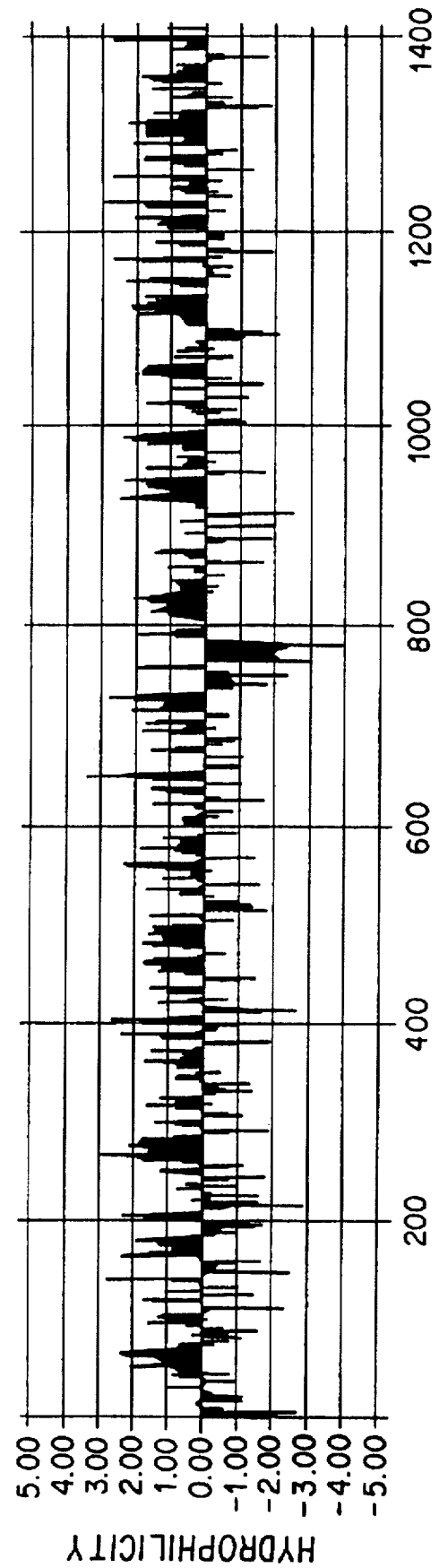
FIG. 8 depicts a hydropathy plot of the predicted amino acid sequence for the KDR protein.

DNA sequencing of BTIII081.8, BTIII129.5 and BTTV169 (SEQ ID NO. 7) shows that the newly isolated gene is similar to, but distinct from, previously identified type III RTK. The predicted amino acid sequence (SEQ ID NO. 7) contains several structural features which demonstrate that the novel gene is a type III RTK. These structural features are summarized as follows:

1) A hydropathy plot of the predicted amino acid sequence indicates a single membrane spanning region (see FIG. 8). This is characteristic of a type III RTK (FIG. 7).

2) The putative amino-terminal 762 amino acid portion of the receptor has structural features of extracellular receptor ligand binding domains (1), including regularly spaced cysteines and 18 potential N-linked glycosylation sites (FIG. 7).

3) The predicted amino acid sequence of the carboxy-terminal 530 amino acid portion contains an ATP-binding site at lysine 868, 22 amino acids downstream from the consensus ATP recognition sequence Gly-X-Gly-X-X-Gly (26) (FIG. 8).

4) Within the kinase domain there is a 55-60% identical match in amino acid sequence to three other type III receptor tyrosine kinases: ckit proto-oncogene (SEQ ID NO: 8), CSF-1 (SEQ ID NO: 9) and PDGF (SEQ ID NO: 10) (FIG. 9).

5) The predicted kinase domain contains a kinase insert domain of approximately 71 amino acids. As indicated in FIG. 9, this portion of the amino acid sequence shares little sequence homology with other type III RTK.

The endothelial cell library can be further screened to isolate the 5' untranslated region and genomic clones can be generated so as to isolate the promoter region for the KDR gene.

In addition to the DNA sequence described for the KDR gene (SEQ ID NO. 7), the present invention further comprises DNA sequences which, by virtue of the redundancy of the genetic code, are biologically equivalent to the sequences which encode for the receptor, that is, these other DNA sequences are characterized by nucleotide sequences which differ from those set forth herein, but which encode a receptor having the same amino acid sequences as those encoded by the DNA sequences set forth herein.

In particular, the invention contemplates those DNA sequences which are sufficiently duplicative of the sequence of SEQ ID NO. 7 so as to permit hybridization therewith under standard high stringency Southern hybridization conditions, such as those described in Sambrook et al. (27), as well as the biologically active proteins produced thereby.

This invention also comprises DNA sequences which encode amino acid sequences which differ from those of the novel receptor, but which are the biological equivalent to those described for the receptor. Such amino acid sequences may be said to be biologically equivalent to those of the receptor if their sequences differ only by minor deletions from or conservative substitutions to the receptor sequence, such that the tertiary configurations of the sequences are essentially unchanged from those of the receptor.

For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, as well as changes based on similarities of residues in their hydropathic index, can also be expected to produce a biologically equivalent product. Nucleotide changes which result in alteration of the N-terminal or C-terminal portions of the protein molecule would also not be expected to alter the activity of the protein. It may also be desirable to eliminate one or more of the cysteines present in the sequence, as the presence of cysteines may result in the undesirable formation of multimers when the protein is produced recombinantly, thereby complicating the purification and crystallization processes. Each of the proposed modifications is well within the routine skill in the art, as is determination of retention of biological activity of the encoded products. Therefore, where the terms "KDR gene" or "KDR protein" are used in either the specification or the claims, each will be understood to encompass all such modifications and variations which result in the production of a biologically equivalent protein.

In addition to the full length gene and protein, the invention encompasses biologically active fragments of each. By "biologically active" is meant a protein fragment which qualitatively retains the receptor activity of the larger KDR protein, or, in the case of a nucleotide sequence, which encodes such a protein fragment. It also refers, for purposes of antibody production, to fragments which are capable of eliciting production of antibodies capable of binding to the receptor protein.

Figure 10:
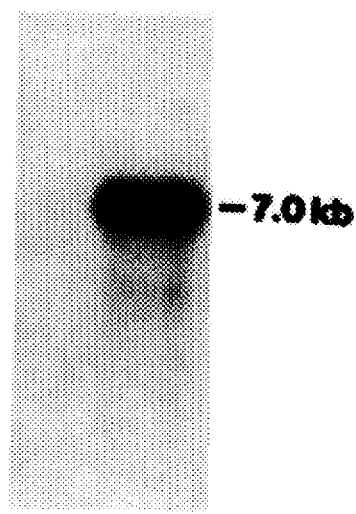
FIG. 10 depicts the identification of kdp receptor mRNA by Northern blot analysis. Five micrograms of bovine aortic endothelial cell polyA+ RNA are used. A nick-translated [$^{32}$P] CTP-labelled EcoRI/BamHI DNA segment (nucleotides 1510–2417 of SEQ ID NO: 7) is used as a probe. Autoradiography is for 36 hours.

To determine the size of the mRNA transcribed from the kdp gene, Northern blot hybridization experiments are carried out using an EcoRI/BamHI DNA segment (nucleotides 1510-2417, SEQ ID NO. 7) as a hybridization probe. The DNA used for the probe does not contain any portion of the putative kinase domain, and shares little sequence homology to other tyrosine kinases. The Northern blot analysis (FIG. 10) shows that a 7 kb band is visualized in cytoplasmic poly(A)+ RNA of ABAE bovine aortic endothelial cells. This transcript differs in size from previously reported transcripts for known type III RTK (7,18).

The isolated cDNA is significant for several reasons. The cDNA encodes a novel type III receptor tyrosine kinase. The homology between the sequence of this cDNA and that of other receptors, as well as structural properties implied by the predicted amino acid sequence confirm the relationship. Receptors for growth factors should have tremendous utility in drug development as they face the outside of the cell and thus are among the best targets for drugs. In addition, the cellular levels of some receptors, in particular the neu proto-oncogene, increase during some cancers. This has been taken advantage of in designing diagnostic tests for these cancers.

Figure 11:
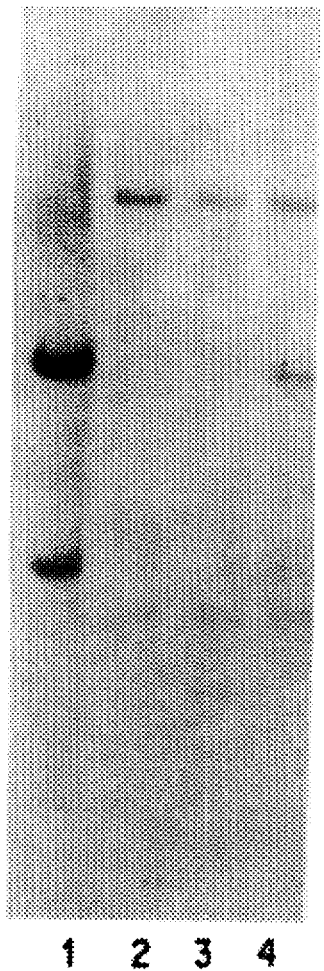
FIG. 11 depicts the kdp gene in human and mouse DNA by Southern blot analysis. A nick translated [$^{32}$P]CTP-labelled EcoRI/BamHI DNA segment (nucleotides 1510–2417 of SEQ ID NO: 7) is used as the probe. The probe is hybridized to Southern blots containing EcoRI digested DNA from human (lane 1), mouse (lane 2), and human-mouse hybrid cells (19) (lanes 3 and 4). The DNA used in lane 3 lacks the kdp locus, while DNA used in lane 4 contains the kdp locus.

Southern analysis demonstrates that the kdp gene is present in mouse as well as human DNA. Mouse and human (Hela cell) DNA, 15 mg of each, are digested with 10 units of EcoRI and electrophoresed on a 0.7% agarose gel. The DNA is transferred onto nitrocellulose. The filter is hybridized to a [$^{32}$P]CTP-labelled cDNA probe made by nick translating an EcoRI/BamHI fragment from the 5' end of the kdp cDNA (nucleotides 1510–2417, SEQ ID NO. 7). Hybridization is conducted at 30° C. in 5×SSPE, 50% formamide, 0.1% SDS, plus 150 mg/ml salmon sperm DNA. The DNA probe hybridizes to Southern blots containing EcoRI digested DNA. After 48 hours, the filter is washed at room temperature in 2×SSC plus 0.1% SDS for 20 minutes, followed by two 20 minute washes at 40° C. with 0.1×SSC plus 0.1% SDS. Autoradiography is then performed for 48 hours. As shown in FIG. 11, radioactively labelled DNA is present in both human and mouse samples. This indicates that the kdp gene is present in both species.

An experiment is conducted to ascertain the genetic locus of kdp on human chromosomes. Thirty-eight cell hybrids from 18 unrelated human cell lines and four mouse cell lines are examined (19). A DNA probe hybridizes to Southern blots which contain EcoRI digested DNA from the human-mouse hybrids (using the procedure and DNA probe for human and mouse tissue described in relation to FIG. 11). Table I sets forth the results of the segregation of kdp with human chromosomes in EcoRI digested human-mouse somatic cell hybrid DNA:

TABLE I

| Chromosome | Concordant # of Hybrids (+/+) | Concordant # of Hybrids (−/−) | Discordant # of Hybrids (+/−) | Discordant # of Hybrids (−/+) | % Discordancy |
|---|---|---|---|---|---|
| 1 | 4 | 19 | 8 | 4 | 34 |
| 2 | 8 | 18 | 5 | 6 | 30 |
| 3 | 11 | 12 | 3 | 9 | 34 |
| 4 | 14 | 24 | 0 | 0 | 0 |
| 5 | 7 | 14 | 7 | 10 | 45 |
| 6 | 7 | 19 | 7 | 5 | 32 |
| 7 | 11 | 14 | 3 | 8 | 31 |
| 8 | 8 | 11 | 6 | 13 | 50 |
| 9 | 3 | 20 | 10 | 4 | 38 |
| 10 | 12 | 9 | 2 | 14 | 43 |
| 11 | 9 | 13 | 4 | 11 | 41 |
| 12 | 9 | 10 | 5 | 14 | 50 |
| 13 | 7 | 18 | 7 | 6 | 34 |
| 14 | 11 | 8 | 3 | 16 | 50 |
| 15 | 9 | 15 | 5 | 8 | 35 |
| 16 | 7 | 19 | 7 | 5 | 32 |
| 17 | 12 | 7 | 2 | 16 | 49 |
| 18 | 11 | 14 | 3 | 10 | 34 |
| 19 | 7 | 18 | 7 | 6 | 34 |
| 20 | 9 | 10 | 5 | 14 | 50 |
| 21 | 11 | 9 | 3 | 15 | 47 |
| 22 | 3 | 16 | 10 | 7 | 47 |
| X | 8 | 10 | 3 | 8 | 38 |

The scoring is determined by the presence(+) or absence (−) of human bands in the hybrids on Southern blots prepared in a similar to those shown in FIG. 11. The scoring is compared to the presence or absence of human chromosomes in each hybrid. A 0% discordancy indicates a matched segregation of the DNA probe with a chromosome. Three fragments, approximately 6.5 kb, 3.1 kb, and 0.7 kb in size are detected in digests of human DNA (FIG. 11), and in all hybrids which had retained human chromosome 4 (Table I). All other chromosomes are excluded in at least 11 discordant hybrids (Table I). The results of FIG. 11 and Table I demonstrate that the genetic locus of kdp is on human chromosome 4.

It is noteworthy that both the ckit (3) and the type A PDGF (28) receptor genes map to human chromosome 4. The finding that the genetic locus of kdp is on human chromosome 4 provides further evidence that the novel receptor of this invention is a type III receptor tyrosine kinase.

The next step after identifying the entire coding portion of the kdp gene is to express the receptor protein encoded by that gene. The receptor protein is then utilized so as to identify the growth factor which binds specifically to the receptor.

The receptor protein is expressed using established recombinant DNA methods. Suitable host organisms include bacteria, viruses, yeast, insect or mammalian cell lines, as well as other conventional organisms. For example, CMT-3 monkey kidney cells are tranfected with a vector containing the complete coding region of the KDR gene.

The complete coding portion of the KDR gene is assembled by sequentially cloning into pUC119 three DNA fragments derived from BTIII081.8, BTIII129.5, and BTIV169. First, a SmaI-EcoRI fragment of clone BTIII129.5 (nucleotides 3152–4236, SEQ ID NO: 7) is blunt ended with Klenow polymerase and introduced into a SmaI site in pUC119. Next, a BamHI-SmaI fragment of clone BTIII081.8 (nucleotides 2418–3151, SEQ ID NO: 7) is introduced at a BamHI-SmaI site. Finally, a SalI-BamHI fragment of clone BTIV169 (nucleotides 1–2417, SEQ ID NO: 7) is introduced at a SalI-BamHI site. Part of the cloning site of pUC119 is contained in the SalI-BamHI fragment, 5' to the KDR gene. In order to clone the complete coding portion into an expression vector, the assembled DNA (in pUC119) is digested with SalI and Asp118 and recloned into the eukaryotic expression vector pcDNA1tkpASP.

This vector is a modification of the vector pcDNA1 (Invitrogen; San Diego, Calif.). Specifically, the ampicillin resistance gene is cloned from pBR322 into pcDNA1. A small SV40 T splice and the SV40 polyadenylation signal are then removed and are replaced with a Herpes Simplex Virus-1 polyadenylation signal. Finally, a cytomegalovirus intermediate early splice is inserted 5' to the cloning site to yield pcDNA1tkpASP.

Transfection of CMT-3 cells is done using DEAE-dextran. Forty-eight hours after transfection, expression of the novel receptor is monitored using Western blot analysis as follows.

An antibody is used to assay the expressed receptor protein. The predicted amino acid sequence of the receptor is used to generate peptide-derived antibodies to the receptor by conventional techniques. The presence of the novel receptor protein is confirmed by Western blot hybridization.

Specifically, a synthetic peptide with 13 residues is synthesized based on the 12 residues corresponding to amino acids 986–997 of the putative amino acid sequence of the KDR protein (SEQ ID NO: 7), with a cysteine residue linked to the lysine (amino acid 997). The cysteine facilitates coupling of the peptide to a macromolecule which functions as a carrier for the peptide. For example, the peptide is coupled to keyhole limpet haemocyanin (KLH) using m-maleimidobenzoyl-N-hydroxysuccinimide ester. Other conventional carriers may be used such as human and bovine serum albumins, myoglobins, b-galactosidase, penicillinase and bacterial toxoids, as well as synthetic molecules such as multi-poly-DL-alanyl-poly-L-lysine and poly-L-lysine.

Rabbits are immunized with the peptide-KLH conjugate to raise polyclonal antibodies. After different periods of time, serum is collected from the rabbits. The IgG fraction of the serum is then purified using a protein A Sepharose column (Pharmacia LKB, Uppsala, Sweden) to obtain the antibody which is designated anti-KDR.PS23.

A sample of the expressed KDR protein is subjected to SDS-PAGE using a 7% acrylamide gel under standard conditions. The protein band is then transferred onto nitrocellulose paper for Western blot analysis and the anti-KDR.PS23 antibody is added at a dilution of 1:1,000 to allow the antibody to react with the protein present. A second antibody, goat anti-rabbit antibody to rabbit IgG, which binds to anti-KDR.PS23, is then added. The detection of proteins which react with the antibodies is performed by autoradiography of bands using an ECL system (Amersham, Chicago, Ill.). The results are depicted in FIG. 12.

Figure 12:
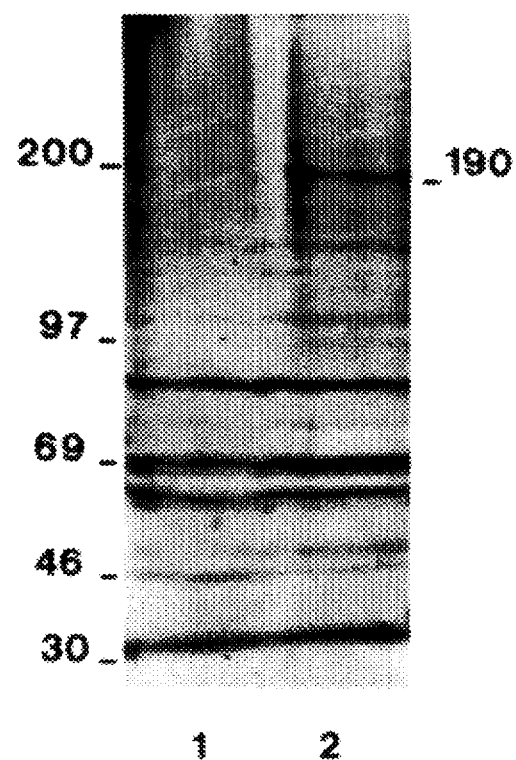
FIG. 12 depicts a Western blot analysis of CMT-3 cells which express the KDR protein. Cells are transfected with either the pcDNAItkpASP vector alone (lane 1) or with that vector modified to contain the KDR gene (lane 2). 2×10$^5$ cells and 1 microgram of DNA are used for each transfection. Forty-eight hours later, Western blot analysis is performed on the samples using the anti-KDR.PS23 polyclonal antibody at a dilution of 1:1000. Detection of reacting proteins is performed using an ECL system (Amersham, Chicago, Ill.).

FIG. 12 shows that a 190 kD protein is present in the cells transfected with the vector containing the KDR gene, but is absent in cells transfected with vector alone. The size of this protein is consistent with it being encoded by the KDR gene, in that the predicted amino acid sequence for the unglycosylated KDR protein is 156 kD, and that sequence contains 18 putative extracellular glycosylation sites which would account for the balance of the size seen in the 190 kD band.

The expressed receptor is then used to identify the growth factor which interacts with the receptor. In order to test the hypothesis that the KDR protein is a receptor for VEGF, radioligand binding studies are performed. VEGF (provided by D. Gospodarowicz) is radiolabelled with $^{125}$I. Cells are transfected with either the vector pcDNA1tkpASP alone (bars 1 and 2 of FIG. 13) or with the vector containing the KDR gene (bars 3 and 4). Forty-eight hours later, the transfected cell samples are washed with PBS and then incubated for 90 minutes with serum-free media containing 50 pM [$^{125}$I]VEGF (specific activity equal to 4,000 cpm per fmol). Excess nonradioactive VEGF, 5 nM, is added to some samples (bars 2 and 4) to define specific binding sites. The samples are washed with ice cold PBS, and the cells are transferred to gamma-counting tubes using a detergent, 0.1% lubrol.

Figure 13:
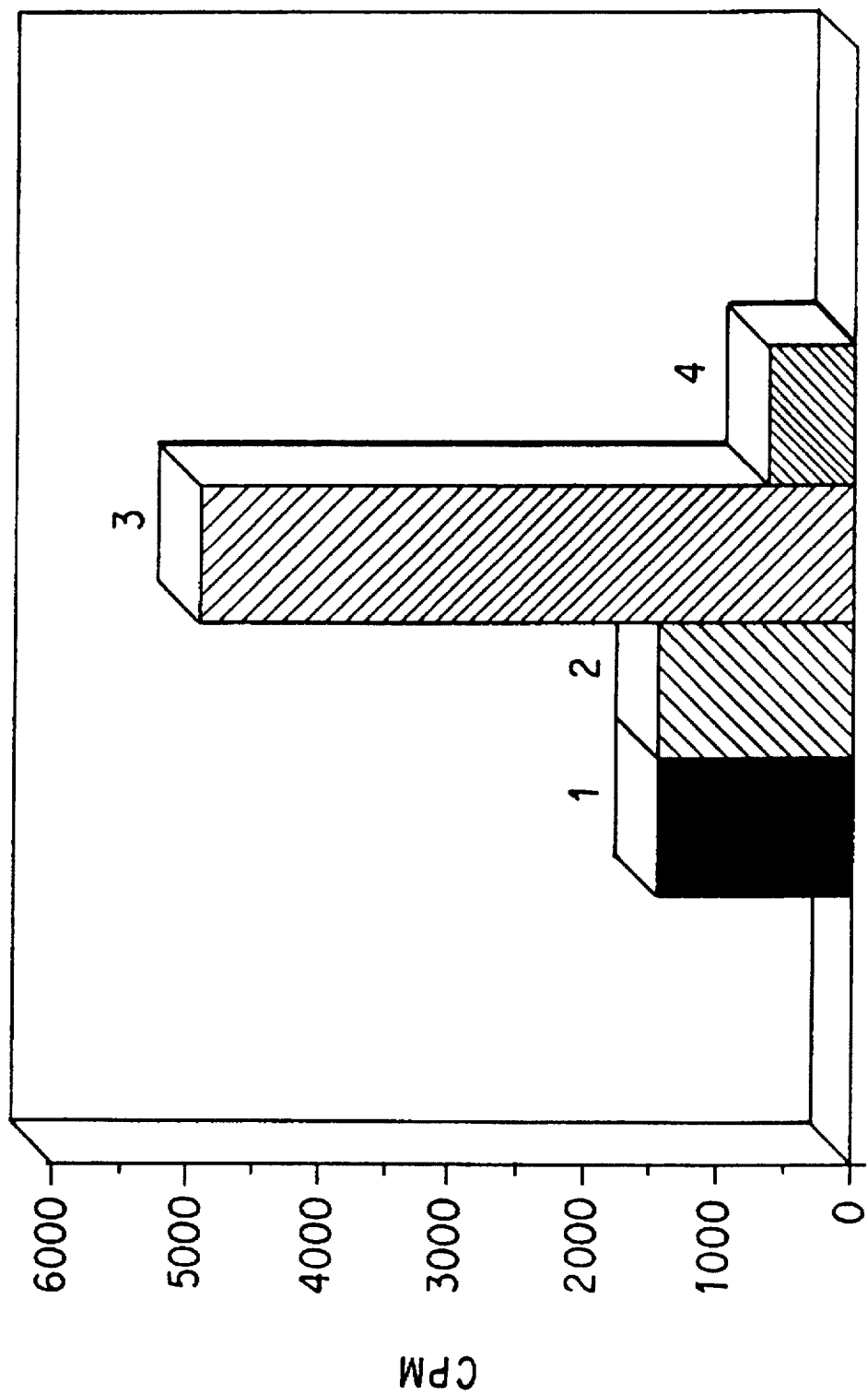
FIG. 13 depicts the results of [$^{125}$I] VEGF binding to CMT-3 cells which express the KDR protein. Cells are transfected with either the vector alone (bars 1 and 2) or with the vector containing the KDR gene (bars 3 and 4). Forty-eight hours later, the samples are washed with phosphate buffered saline (PBS), and incubated with serum-free media containing 50 pM [$^{125}$I] VEGF (specific activity equal to 4,000 cpm per fmol), for 90 minutes. Nonradioactive VEGF, 5 nM, is added to some samples (bars 2 and 4) to define specific binding sites. The samples are washed with ice cold PBS, and the cells are transferred to gamma-counting tubes using 0.1% lubrol.

The results of the radioligand binding studies are depicted in FIG. 13. FIG. 13 shows that CMT-3 cells transfected with vector containing the KDR gene contain specific binding sites for [$^{125}$I]VEGF (compare bars 3 and 4), while cells transfected with vector alone do not (compare bars 1 and 2).

Figure 14:
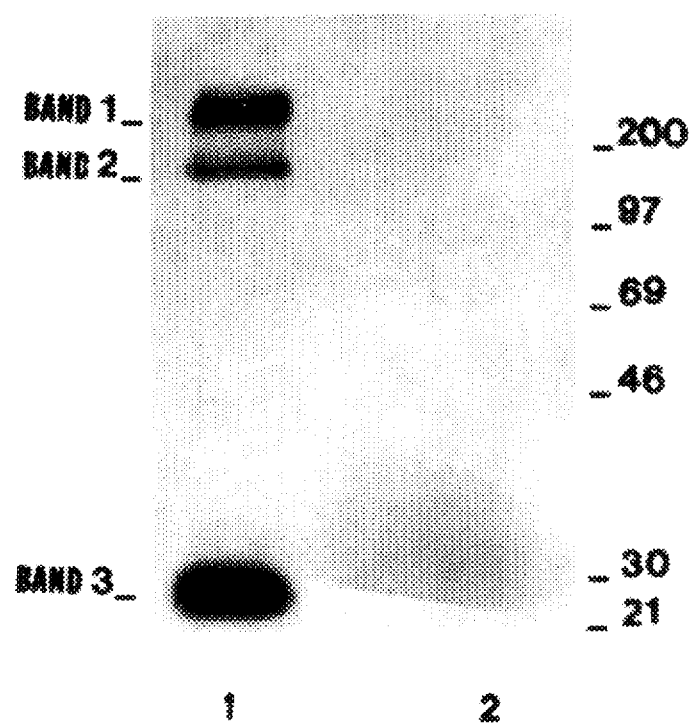
FIG. 14 depicts the results of affinity cross-linking of [$^{125}$I] VEGF to CMT-3 cells which express the KDR protein. CMT-3 cells are transfected with either the vector alone (lane 1) or with the vector containing the KDR gene (lane 2). Forty-eight hours later, the cells are washed in PBS, and serum free media containing 200 pM [$^{125}$I] VEGF is added. After 90 minutes at room temperature, an affinity cross-linker disuccinimidyl suberate, 0.5 mM, is added for 15 minutes. The samples are then prepared for SDS-PAGE autoradiography.

Further evidence that the KDR gene encodes a receptor for VEGF is demonstrated by affinity cross-linking studies (FIG. 14). FIG. 14 depicts the results of affinity cross-linking of [$^{125}$I]VEGF to CMT-3 cells which express the KDR protein. CMT-3 cells are transfected with either the pcDNA1tkpASP vector alone (lane 1 of FIG. 14) or with the vector containing the KDR gene (lane 2). Forty-eight hours later, the cells are washed in PBS, and serum free media containing 200 pM [$^{125}$I]VEGF is added. After 90 minutes at room temperature, an affinity cross-linker disuccinimidyl suberate (Pierce Biochemicals, Rockford, Ill.), 0.5 mM, is added for 15 minutes. The samples are then subjected to SDS-PAGE autoradiography.

Three protein bands are seen in SDS-PAGE autoradiograms from samples of CMT-3 cells transfected with the KDR gene and cross-linked to [$^{125}$I]VEGF (lane 1). The size of band 1 (235 kD) is consistent with it being the 190 kD protein seen by Western blot analysis (FIG. 12), because a 45 kD [$^{125}$I] VEGF dimer plus 190 kD would migrate in a manner identical to band 1. The origin of band 2 is not clear, but may represent an altered glycosylation form of band 1. Band 3 (22.5 kD) is most likely VEGF itself, and can be seen faintly in cells transfected with vector alone (lane 2).

The novel KDR gene of this invention is significant for several reasons. Studies of the cellular mechanisms by which receptors function in signal transduction have led in the past to a better understanding of how cells grow in both normal and diseased states. Receptor tyrosine kinases, in particular, have received a great deal of attention because of the observation that a number of RTK are the cellular counterparts for viral oncogenes, implying a direct correlation between changes in the expression of RTK and cancer. In view of this, it is likely that pharmaceuticals targeted at RTK will inhibit the changes in cell growth associated with cancer. In additon, it is likely that monitoring the levels of expression of RTK will prove valuable in diagnosing the onset of cancer.

The described cDNA is isolated from a human endothelial cell library. Endothelial cells participate in angiogenesis, the formation of new blood capillaries. Previous work directed towards identifying the growth factors which regulate angiogenesis have primarily focused upon FGF (13), although recent evidence has indicated that other growth factors may be involved as well (12,15,29). This evidence consists of the observations that: 1) FGF does not contain a signal sequence (24) and thus may not be secreted from cells in a manner con stent with the tight regulation of angiogenesis, and 2) endothelial cells synthesize FGF and yet are normally resting (15). Our discovery, then, of a novel growth factor receptor may ultimately clarify these inconsistencies and lead to a better understanding of endothelial cell function.

The teachings of this invention can be readily used by those skilled the art for the purpose of testing pharmaceuticals targeted at the KDR protein. Two examples of approaches which can be used for this purpose are now given.

First, the methods described in this invention for studying the interaction of VEGF with KDR protein can be used to test for pharmaceuticals which will antagonize that interaction. For these studies, cells expressing the KDR protein are incubated with [$^{125}$I]VEGF, together with a candidate pharmaceutical. Inhibition of radioligand binding is tested for; significant inhibition indicates the candidate is an antagonist. Permanen expression of the KDR protein in a cell type such a NIH3T3 cells would make these studies less laborious. This can be easily achieved by those skilled in the art using the described methods.

Second, using the teachings of this invention, those skilled in the art can study structural properties of the KDR protein involved in receptor function. This structural information can then be used to more rationally design pharmaceuticals which inhibit that function. Mutagenesis of the KDR gene by well established protocols is one approach, crystallization of the receptor binding site is another.

BIBLIOGRAPHY

1. Yarden Y., and A. Ullrich, *Ann. Rev. Biochem.*, 57, 433–478 (1988).
2. Bargmann, C., et al., *Nature*, 319, 226–230 (1986).
3. Yarden, Y., et al., *EMBO J.*, 6, 3341–3351 (1987).
4. Coussens, L., et al., *Nature*, 320, 277–280 (1986).
5. Slamon, D., et al., *Science*, 244, 707–712 (1989).
6. Ullrich, A. and Schlessinger, J., *Cell*, 61, 203–212 (1990).
7. Ruta, M., et al., *Oncogene*, 3, 9–15 (1988).
8. Strathmann, M., et al., *Proc. Natl. Acad. Sci.*, 86, 8698–8702 (1989).
9. Streuli, M., et al., *Proc. Natl. Acad. Sci.*, 86, 8698–8702 (1989).
10. Wilkes, A. F., *Proc. Natl. Acad. Sci.*, 86, 1603–1607 (1989).
11. Folkman, J., and Klagsbrun, M., *Science*, 235, 442–445 (1987).

12. Ishikawa, F., et al., *Nature*, 338, 557–562 (1989).

13. Baird, A., and Bohlen, P., in *Peptide Growth Factors and Their Receptors*, pages 369–418 (Spron, M. B., and Roberts, A. B., eds. 1990).

14. Senger, D. R., et al., *Science*, 219, 983–985 (1983).

15. Gospodarowicz, D., et al., *Proc. Natl. Acad. Sci.*, 86, 7311–7315 (1989).

16. Leung, D. W., et al., *Science*, 246, 1306–1309 (1989).

17. Maglione, D., et al., *Proc. Natl. Acad. Sci.*, 88, 9267–9271 (1991).

18. Gronwald, R., et al., *Proc. Natl. Acad. Sci.*, 85, 3435–3439 (1988).

19. Shows, T., et al., *Somat. Del. Mol. Gen.*, 10, 315–318 (1984).

20. Rainer, G., et al., *Proc. Natl. Acad. Sci.*, 85, 3435–3439 (1988).

21. Lee, P. L., et al., *Science*, 245, 57–60 (1989).

22. Sanger, F., et al., *Proc. Natl. Acad. Sci.*, 74, 5463–5467 (1977).

23. Folkman, J., *Cancer Res.*, 46, 467–473 (1986).

24. Burgess, W. and Maciag, T., *Ann. Rev. Biochem.*, 58, 575–606 (1989).

25. Matthews, W., et al., *Proc. Natl. Acad. Sci.*, 88, 9026–9030 (1991).

26. Hannink, M. and Donoghue, D., *Proc. Natl. Acad. Sci.*, 82, 7894–7898 (1985).

27. Sambrook, J., et al., *Molecule Cloning: A Laboratory Manual*, 2nd ed., Cold Spring Harbor Laboratory Press, Cold Spring Harbor, N.Y. (1989).

28. Matsui, T., et al., *Science*, 243, 800–804 (1989).

29. Conn, G., et al., *Proc. Natl. Acad. Sci.*, 87, 2628–2632 (1990).

---

We claim:

1. A screening method to identify compounds that inhibit the action of vascular endothelial cell growth factor (VEGF) on a human Kinase insert Domain containing Receptor (KDR) encoded by a nucleic acid sequence comprising SEQ ID NO: 7, comprising the steps of:

(a) incubating cells which have been transformed or transfected to express the KDR with [$^{125}$I]VEGF and a compound;

(b) measuring the emitted radioactivity to determine the amount of inhibition of binding of VEGF to the KDR by the compound.

\* \* \* \* \*